US011359182B2

(12) United States Patent
Boyle et al.

(10) Patent No.: US 11,359,182 B2
(45) Date of Patent: Jun. 14, 2022

(54) PROTECTIVE ENZYMES

(71) Applicant: Ginkgo Bioworks, Inc., Boston, MA (US)

(72) Inventors: Patrick Magannig Boyle, Boston, MA (US); Jeffrey Ian Boucher, Boston, MA (US); Michael Gregory Napolitano, Boston, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

(21) Appl. No.: 16/646,814

(22) PCT Filed: Sep. 12, 2018

(86) PCT No.: PCT/US2018/050718
§ 371 (c)(1),
(2) Date: Mar. 12, 2020

(87) PCT Pub. No.: WO2019/055541
PCT Pub. Date: Mar. 21, 2019

(65) Prior Publication Data
US 2020/0255809 A1 Aug. 13, 2020

Related U.S. Application Data

(60) Provisional application No. 62/557,544, filed on Sep. 12, 2017.

(51) Int. Cl.
*C12N 15/74* (2006.01)
*C12N 9/02* (2006.01)

(52) U.S. Cl.
CPC ................. *C12N 9/0069* (2013.01)

(58) Field of Classification Search
CPC .......... C12N 15/74; C12N 15/52; C12P 7/065
See application file for complete search history.

(56) References Cited

U.S. PATENT DOCUMENTS

| | | | |
|---|---|---|---|
| 5,520,727 | A | 5/1996 | Vreeland et al. |
| 7,348,173 | B2 | 3/2008 | Gilula et al. |
| 8,394,618 | B2 | 3/2013 | Buthe et al. |
| 8,932,717 | B2 | 1/2015 | Lee et al. |
| 9,564,966 | B1 | 2/2017 | Breuer et al. |
| 9,615,475 | B2 | 4/2017 | Bae et al. |
| 9,686,874 | B2 | 6/2017 | Jeon et al. |
| 2003/0124710 | A1 | 7/2003 | Borch et al. |
| 2010/0196991 | A1 | 8/2010 | O'Connell et al. |
| 2010/0210745 | A1 | 8/2010 | McDaniel et al. |
| 2013/0129653 | A1 | 5/2013 | Castiel et al. |
| 2013/0329460 | A1 | 12/2013 | Mathew et al. |
| 2014/0091536 | A1 | 4/2014 | Bae et al. |
| 2014/0193889 | A1 | 7/2014 | McDaniel |
| 2015/0177790 | A1 | 6/2015 | Uto et al. |
| 2015/0184208 | A1 | 7/2015 | Oestergaard et al. |
| 2016/0186018 | A1 | 6/2016 | Mikkonen |
| 2017/0093489 | A1 | 3/2017 | Breuer et al. |
| 2018/0077813 | A1 | 3/2018 | Lancaster-Larocque et al. |

FOREIGN PATENT DOCUMENTS

| | | |
|---|---|---|
| WO | WO 2008/056291 A2 | 5/2008 |
| WO | WO 2009/155115 A | 12/2009 |
| WO | WO 2013/109934 A1 | 7/2013 |

OTHER PUBLICATIONS

Gen Bank Accession No. CP003614 residues 5069506 to 5071152 (Year: 2013).*
International Search Report and Written Opinion dated Dec. 19, 2018 for Application No. PCT/US2018/050718.
International Preliminary Report on Patentability dated Mar. 26, 2020 for Application No. PCT/US2018/050718.
Alestas et al., Enzymes involved in the biosynthesis of leukotriene B4 and prostaglandin E2 are active in sebaceous glands. J Mol Med (Berl). Jan. 2006;84(1):75-87. Epub Dec. 31, 2005.
Bodalo et al., Production of (E) 10-hydroxy-8-octadecenoic acid with lyophilized microbial cells. Amer. J. Biochem. Biotechnol. 2005;1(1):1-4.
Busquets et al., Isolation and characterization of a lipoxygenase from Pseudomonas 42A2 responsible for the biotransformation of oleic acid into ( S )-( E)-10-hydroxy-8-octadecenoic acid. Antonie Van Leeuwenhoek. Feb. 2004;85(2):129-39. Erratum in: Antonie Van Leeuwenhoek. Aug. 2004;86(2):201.
Gillmor et al., The structure of mammalian 15-lipoxygenase reveals similarity to the lipases and the determinants of substrate specificity. Nat Struct Biol. Dec. 1997;4(12):1003-9. Erratum in: Nat Struct Biol Mar. 1998;5(3):242.
Graf et al., Random circular permutation of genes and expressed polypeptide chains: application of the method to the catalytic chains of aspartate transcarbamoylase. Proc Natl Acad Sci U S A. 1996;93(21):11591-11596. doi:10.1073/pnas.93.21.11591.
Hatamleh et al., Effect of extraoral aging conditions on mechanical properties of maxillofacial silicone elastomer. J Prosthodont. Aug. 2011;20(6):439-46. doi: 10.1111/j.1532-849X.2011.00736.x. Epub Jul. 20, 2011.
Heshof et al., Industrial potential of lipoxygenases. Crit Rev Biotechnol. Aug. 2016;36(4):665-74. doi: 10.3109/07388551.2015.1004520. Epub Feb. 2, 2015.
McDaniel, Bioengineered Additives: A Pipeline of Value Delivering Unique Functionality to Your Coating. Coatings World. May 2010; 10 pages.
Rawlins et al., Putting nature to work. Eur Coating J. 2008;11(9 pages).

(Continued)

*Primary Examiner* — Tekchand Saidha
(74) *Attorney, Agent, or Firm* — Wolf, Greenfield & Sacks, P.C.

(57) ABSTRACT

The present invention relates to methods and compositions that include enzymes and/or binding polypeptides useful for protecting polymers from damage caused by fatty acids from secreted biological fluids such as sebum or sweat.

11 Claims, 5 Drawing Sheets
Specification includes a Sequence Listing.

(56) References Cited

OTHER PUBLICATIONS

Snabe et al., Enzymatic lipid removal from surfaces-lipid desorption by a pH-induced "electrostatic explosion". Chem Phys Lipids. Jan. 2005;133(1):37-49.
Tayeb et al., Effect of Lipoxygenase Oxidation on Surface Deposition of Unsaturated Fatty Acids. Langmuir. May 9, 2017;33(18):4559-4566. doi: 10.1021/acs.langmuir.7b00908. Epub Apr. 29, 2017.
Williams et al., How bio-engineered additives can lead to self-degreasing laminates. Polym., Paint Colour J. 2011;(201):36-37.

* cited by examiner

PROTECTIVE ENZYMES

CROSS REFERENCE TO RELATED APPLICATIONS

The present application is a national stage filing under 35 U.S.C. § 371 of international PCT application PCT/US2018/050718, filed Sep. 12, 2018, entitled "PROTECTIVE ENZYMES," which was published under PCT Article 21(2) in English and which claims the benefit under 35 U.S.C. § 119(e) of U.S. Provisional Application No. 62/557,544, filed Sep. 12, 2017, the entire contents of each of which are herein incorporated by reference in their entireties.

SEQUENCE LISTING

The present specification makes reference to a Sequence Listing (submitted electronically as a .txt file named "G091970029US01-SEQ-OMJ"). The .txt file was generated on Mar. 12, 2020, and is 74 kilobytes in size. The entire content of the Sequence Listing is herein incorporated by reference.

BACKGROUND

Polymeric materials may be vulnerable to degradation from contaminants.

SUMMARY

The present disclosure encompasses the recognition that certain enzymes and polypeptides may be useful to neutralize (e.g., prevent or mitigate) damage to polymeric compositions caused by lipids. Exposure to certain secreted biological fluids containing lipids (e.g., human sweat and skin oils) can cause some polymers to swell and degrade. In some embodiments, an enzyme of the present disclosure facilitates degradation of a lipid, and thereby prevents damage to a polymeric structure. In some embodiments, an enzyme useful in the context of the present disclosure facilitates degradation of harmful lipids such as fatty acids.

The present disclosure provides methods and compositions that protect components of a composition (e.g., polymers) from damage by lipids (e.g., fatty acids) and/or other compounds that may cause damage. In some embodiments, a lipid and/or other compound that may cause damage is present in a biological fluid. In some embodiments methods and compositions are provided that include protective enzymes useful for breakdown of components in biological fluids that may cause damage to a polymer. In some embodiments, methods and compositions are provided where one or more protective enzymes are embedded within a composition. In some embodiments, methods and compositions are provided where one or more protective enzyme are applied to the surface of a composition (e.g., as a coating).

In some embodiments, methods are provided for promoting breakdown of one or more lipids (e.g., fatty acids) in a biological fluid, the method comprising contacting the biological fluid with an enzyme. In some embodiments, a method for promoting breakdown of one or more lipids in a biological fluid comprises contacting the biological fluid with a plurality of enzymes.

In some embodiments, methods are provided for inhibiting swelling of a polymer caused by exposure to a fatty acid, the methods comprising contacting the polymer with an enzyme. In some embodiments, methods comprise contacting the polymer with a plurality of enzymes. In some embodiments, methods comprise embedding a plurality of enzymes within a polymer. In some embodiments, methods comprise coating a polymeric composition with a plurality of enzymes.

In some embodiments, methods are provided for inhibiting swelling of a polymer caused by exposure to a fatty acid. The methods comprise contacting the polymer with a polypeptide that binds the fatty acid. In some embodiments, a polypeptide forms a complex with the fatty acid. In some embodiments, a polypeptide binding to a fatty acid inhibits reactivity of the fatty acid. In some embodiments, a polypeptide binds to a fatty acid, and thereby prevents it from damaging a polymer. In some embodiments, a polypeptide inhibits diffusion of the fatty acid.

In some embodiments, compositions are provided comprising an enzyme embedded in a polymer. In some embodiments, compositions comprise two or more enzymes embedded in a polymer. In some embodiments, compositions comprise a polymer and two or more enzymes that promote breakdown of a fatty acid.

In some embodiments, compositions are provided comprising a polymer and one or more enzymes that promote breakdown of a fatty acid and one or more polypeptides that form a complex with a fatty acid. In some embodiments, a polypeptide binding to a fatty acid inhibits the reactivity of the fatty acid. In some embodiments, a polypeptide binds to a fatty acid, and thereby prevents it from damaging a polymer. In some embodiments, a polypeptide inhibits diffusion of the fatty acid.

In some embodiments, topical formulations are provided comprising one or more enzymes that promote breakdown of a fatty acid. In some embodiments, topical formulations are provided comprising one or more polypeptides that form a complex with a fatty acid.

In some embodiments, compositions are provided comprising one or more enzymes that promote breakdown of a fatty acid and one or more polypeptides that form a complex with a fatty acid. In some embodiments, polypeptide binding to a fatty acid inhibits the reactivity of the fatty acid. In some embodiments, a polypeptide binds to a fatty acid, thereby prevent it from damaging a polymer. In some embodiments, a polypeptide inhibits diffusion of the fatty acid.

In some embodiments, a biological fluid is secreted by a human. In some embodiments, a biological fluid is or comprises human sweat. In some embodiments, a biological fluid is or comprises sebum. In some embodiments, a lipid in a biologic fluid is an unsaturated fatty acid. In some embodiments, unsaturated fatty acids include palmitoleic acid, oleic acid, myristoleic acid, linoleic acid, and/or arachidonic acid. In some embodiments, a fatty acid is an oleic acid. In some embodiments, a fatty acid is a linoleic acid. In some embodiments, a biological fluid comprises a plurality of fatty acids to be neutralized.

In some embodiments, enzymes for use in a method or composition of the present disclosure include dioxygenases, monooxygenases, heme peroxidases, P450s, and combinations and/or variants thereof. In some embodiments, an enzyme is a dioxygenase. In some embodiments, an enzyme is a monooxygenase. In some embodiments, methods comprise contacting the bodily fluid with a plurality of enzymes.

In some embodiments, an enzyme is of animal origin. In some embodiments, an enzyme is of plant origin. In some embodiments, an enzyme is of fungal origin. In some embodiments, an enzyme is of bacterial origin. In some embodiments, an enzyme is a cyanobacterial enzyme. In some embodiments, an enzyme is from archaea.

In some embodiments, an enzyme catalyzes beta or omega oxidation. In some embodiments, an enzyme catalyzes hydroperoxidation at the 10S and/or 12S-carbon of a fatty acid (e.g., an oleic acid). In some embodiments, an enzyme for use in the context of the present disclosure does not require adenosine triphosphate (ATP) for catalytic activity.

In some embodiments, an enzyme is a lipoxygenase and/or has lipoxygenase activity (e.g., 10S-LOX activity). In some embodiments, an enzyme for use in the context of the present disclosure is a cyanobacterial enzyme with LOX activity (e.g., 10S-LOX activity) or variant thereof. In some embodiments, a cyanobacterial prostaglandin-endoperoxide synthase enzyme or variant thereof has LOX activity (e.g., 10S-LOX activity). In some embodiments, a cyanobacterial heme peroxide synthase enzyme or variant thereof has LOX activity (e.g., 10S-LOX activity). In some embodiments, an enzyme with LOX (e.g., 10S-LOX activity) catalytic activity comprises an amino acid sequence of any one of SEQ. ID NOs: 13-15. In some embodiments, an enzyme with LOX (e.g., 10S-LOX activity) catalytic activity comprises an amino acid sequence that is at least about 50% (e.g., at least about 55%, 60%, 65%, 70%, 75%, 80%, 85%, 90%, 95%, 96%, 97%, 98%, or 99%) identical to any one of SEQ ID NOs: 13-15.

In some embodiments, an enzyme is a lipoxygenase. In some embodiments, a lipoxygenase has 10S-LOX activity. In some embodiments, a 10S-LOX comprises an amino acid sequence of any one of SEQ ID NOs: 1-12. In some embodiments, a 10S-LOX enzyme has an amino acid sequence that is at least about 50% (e.g., at least about 55%, 60%, 65%, 70%, 75%, 80%, 85%, 90%, 95%, 96%, 97%, 98%, or 99%) identical to any one of SEQ ID NOs: 1-12. In some embodiments, a 10S-LOX comprises an amino acid sequence of SEQ ID NO: 13. In some embodiments, a 10S-LOX comprises an amino acid sequence of SEQ ID NO: 14. In some embodiments, a 10S-LOX comprises an amino acid sequence of SEQ ID NO: 15. In some embodiments, a 10S-LOX enzyme comprises an amino acid sequence that is at least about 50% (e.g., at least about 55%, 60%, 65%, 70%, 75%, 80%, 85%, 90%, 95%, 96%, 97%, 98%, or 99%) identical to any one of SEQ ID NOs: 13-15. In some embodiments, an enzyme is a lipoxygenase that catalyzes hydroperoxidation at positions 9 and/or 13 of a fatty acid. In some embodiments, an enzyme is a lipoxygenase that catalyzes hydroperoxidation at positions 9S and/or 13S of a fatty acid. In some embodiments, an enzyme is a lipoxygenase that catalyzes hydroperoxidation at positions 9R and/or 13R of a fatty acid.

In some embodiments, an enzyme is embedded in a polymer. In some embodiments, an enzyme is applied to the surface of a polymer. In some embodiments, a polymer is a component of a device. In some embodiments, a device is an electronic device.

BRIEF DESCRIPTION OF THE DRAWINGS

The Drawings included herein, composed of the following Figures, are for illustration purposes only and not for limitation.

CERTAIN DEFINITIONS

Figure 1:
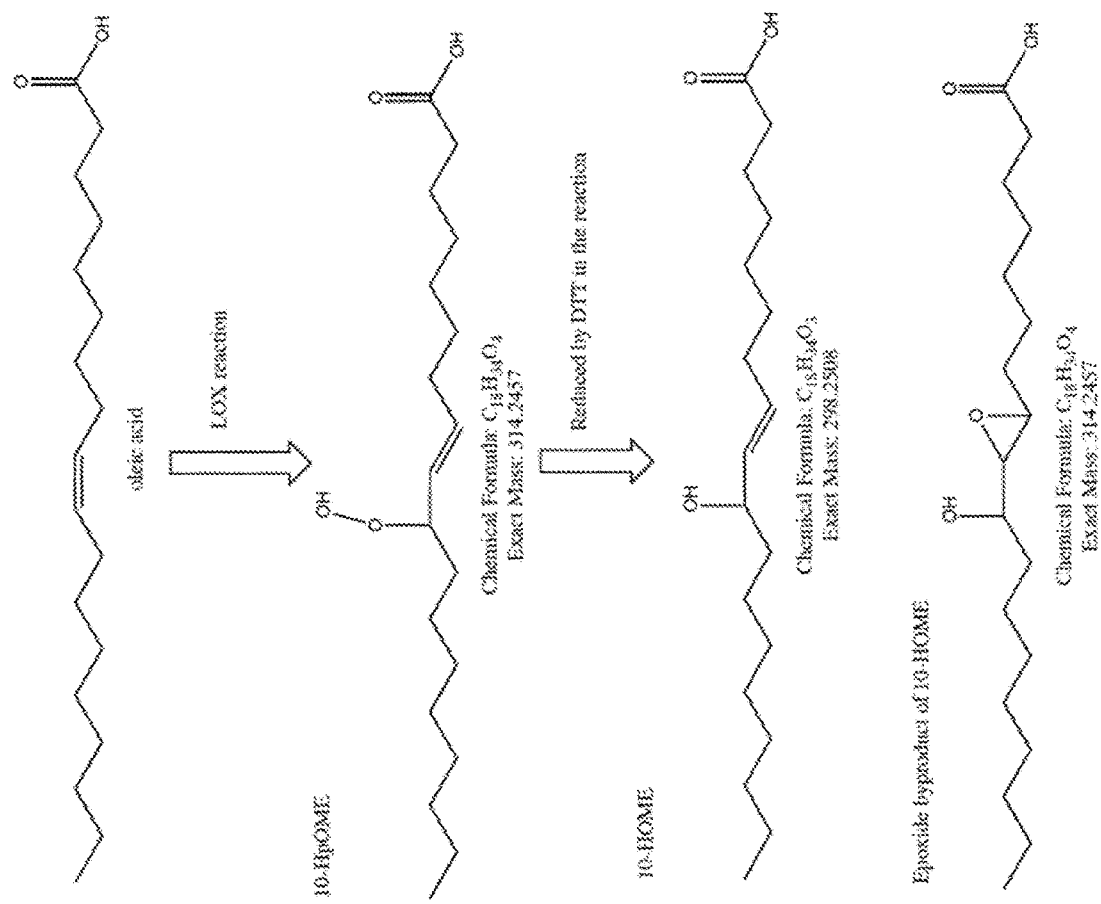
FIG. 1 depicts the chemical reaction catalyzed by LOX enzymes and reduction reaction used to generate a product detected during the enzyme assay.

In order that the present invention may be more readily understood, certain terms are first defined below. Additional definitions for the following terms and other terms are set forth throughout the specification.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Designed: As used herein, the term "designed" refers to an agent (i) whose structure is or was selected by the hand of man; (ii) that is produced by a process requiring the hand of man; and/or (iii) that is distinct from natural substances and other known agents.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Enzyme: As used herein, an "enzyme" is a molecule that catalyzes one or more biochemical reactions. In some embodiments, an enzyme is or comprises a polypeptide and/or RNA. In some embodiments, an enzyme is a polypeptide. In some embodiments, an enzyme is a polypeptide and that ranges from about 50 amino acid residues to 2,500 amino acid residues. Enzymes can be classified according to the reaction they catalyze. In some embodiments, enzymes include oxidoreductases (e.g., catalyze oxidation/reduction reactions), transferases (e.g., transfer a functional group, such as, for example, a methyl or phosphate group), hydrolases (e.g., catalyze hydrolysis of various bonds), lyases (e.g., cleave various bonds by means other than hydrolysis and oxidation), isomerases (e.g., catalyze isomerization changes within a single molecule) and ligases (e.g., join two molecules with covalent bonds). In some embodiments, a member of an enzyme class or family shows significant sequence homology or identity with, shares a common sequence motif (e.g., a characteristic sequence element) with, and/or shares a common activity (in some embodiments at a comparable level or within a designated range) with a reference enzyme of the class; in some embodiments with all enzymes within the class). For example, in some embodiments, a member enzyme shows an overall degree of sequence homology or identity with a reference enzyme that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, an enzyme suitable for use in the context of the present disclosure is of animal origin. In some embodiments, an enzyme suitable for use in the context of the present disclosure is of plant origin. In some embodiments, an enzyme suitable for use in the context of the present disclosure is of fungal origin. In some embodiments, an enzyme suitable for use in the context of the present disclosure is of bacterial origin.

Functional: As used herein, a "functional" biological molecule is a biological molecule in a form in which it exhibits a property and/or activity by which it is characterized.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions).

Human: In some embodiments, a human is an embryo, a fetus, an infant, a child, a teenager, an adult, or a senior citizen.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise D-amino acids, L-amino acids, or both. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a useful polypeptide may comprise or consist of a fragment of a parent polypeptide. The term "peptide" is generally used to refer to a polypeptide having a length of less than about 100 amino acids, less than about 50 amino acids, less than 20 amino acids, or less than 10 amino acids.

Recombinant: As used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source.

DETAILED DESCRIPTION

The present disclosure provides methods and compositions that protect components of a composition (e.g., polymers) from damage by lipids (e.g., fatty acids) and/or other compounds that may cause damage. Also provided herein are compositions, methods, systems, and kits that include a polypeptide and/or an enzyme that catalyzes, degrades, modifies and/or sequesters a lipid.

Enzymes

In some embodiments, provided herein are enzymes useful for breakdown of compounds (e.g., fatty acids) that may cause damage to components of a composition (e.g., polymers). In some embodiments, enzymes for use in the context of the present disclosure include dioxygenases, monooxygenases, heme peroxidases, P450s, and combinations and/or variants thereof. In some embodiments, each of the enzymes can degrade an unsaturated fatty acid. In some embodiments, an enzyme specifically degrades one or more unsaturated fatty acids.

In some embodiments, compositions and methods of the present disclosure comprise two or more enzymes that promote breakdown of compounds that cause damage. In some embodiments, two or more enzymes each promote breakdown of unsaturated fatty acids.

In some embodiments, compositions and methods of the present disclosure comprise a plurality of enzymes. In some embodiments, each of the enzymes can degrade an unsaturated fatty acid. In some embodiments, each of the plurality of enzymes exhibit different substrate specificity for one or more unsaturated fatty acids.

In some embodiments, an enzyme is of animal origin. In some embodiments, an enzyme is of plant origin. In some embodiments, an enzyme is of fungal origin. In some embodiments, an enzyme is of bacterial origin. In some embodiments, an enzyme is a cyanobacterial enzyme. In some embodiments, an enzyme is from archaea.

In some embodiments, an enzyme catalyzes beta or omega oxidation. In some embodiments, an enzyme catalyzes beta or omega oxidation of fatty acids. In some embodiments, an enzyme has activity at the 5, 8, 9, 10, 11, 12, 13 or 15-carbon of a fatty acid. In some embodiments, an enzyme has activity at a 5R, 5S, 8R, 8S, 9R, 9S, 10S, 11R, 11S, 12R, 12S, 13R, 13S and/or 15S position of a fatty acid. In some embodiments, an enzyme has activity at the 10S and/or 12S-carbon of a fatty acid (e.g., an oleic acid). In some embodiments, an enzyme for use in the context of the present disclosure does not require adenosine triphosphate (ATP) for catalytic activity.

In some embodiments, a polymeric composition comprises an enzyme within a range from about 0.0001% to about 20% on w/w basis. In some embodiments, a polymeric composition comprises an enzyme within a range bounded by a lower limit and an upper limit, the upper limit being larger than the lower limit. In some embodiments, the lower limit may be about 0.0001%, 0.0002%, 0.0005%, 0.001%, 0.002%, 0.005%, 0.01%, 0.02%, 0.05%, 0.1%, 0.2%, 0.5%, 1%, 2%, 5%, or 10%. In some embodiments, the upper limit may be about 0.0005%, 0.001%, 0.002%, 0.005%, 0.01%, 0.02%, 0.05%, 0.1%, 0.2%, 0.5%, 1%, 2%, 5%, 10%, or 20%.

Lipoxygenases

In some embodiments, an enzyme for use in the context of the present disclosure is a lipoxygenase. Lipoxygenase (LOX) enzymes catalyze oxygen-dependent oxidation of fatty acid substrates (for example, linoleic acid and arachidonic acid) to form hydroperoxy-fatty acid products. LOX enzymes are categorized as dioxygenases. Certain LOX enzymes have been purified from diverse organisms that display a broad range of substrate specificity and product specificity (e.g., site of oxidation within a fatty acid). LOX enzymes are widely expressed in animals, plants, and fungi, and cyanobacteria.

The present disclosure encompasses the recognition that lipoxygenases are a suitable class of enzymes for the degradation of unsaturated fatty acids (UFA) such as, for example, oleic acid. Without wishing to be bound by theory, LOX enzymes may convert unsaturated fatty acids to hydroperoxides, which can spontaneously degrade at the site of the double bond if not stabilized. In some embodiments, lipoxygenases may utilize either iron or manganese in their active sites.

In some embodiments, a LOX does not require ATP or other cofactors for catalytic activity. The present disclosure encompasses the recognition that activity independent of ATP or other cofactors is a desirable characteristic for certain applications.

In some embodiments, a lipoxygenase suitable for use in the context of the present disclosure is of animal origin. In some embodiments, a lipoxygenase suitable for use in the context of the present disclosure is of plant origin. In some embodiments, a lipoxygenase suitable for use in the context of the present disclosure is of fungal origin. In some embodiments, a lipoxygenase suitable for use in the context of the present disclosure is of bacterial origin. In some embodiments, a lipoxygenase suitable for use in the context of the present disclosure is of cyanobacterial origin. In some embodiments, a lipoxygenase suitable for use in the context of the present disclosure is from archaea.

In some embodiments, a LOX can catalyze hydroperoxidation of a fatty acid substrate. In some embodiments, a fatty acid substrate is an unsaturated fatty acid. In some embodiments, a LOX facilitates catalysis of palmitoleic acid, oleic acid, myristoleic acid, linoleic acid, and/or arachidonic acid.

In some embodiments, a LOX facilitates partial or complete degradation of one or more unsaturated fatty acids. In some embodiments, a LOX facilitates partial or complete degradation of palmitoleic acid, oleic acid, myristoleic acid, linoleic acid, and/or arachidonic acid.

In some embodiments, a LOX has activity (i.e., can catalyze hydroperoxidation) at the 5, 8, 9, 10, 11, 12, 13 or 15-carbon of a fatty acid. In some embodiments, a LOX has activity (i.e., can catalyze hydroperoxidation) at a 5R, 5S, 8R, 8S, 9R, 9S, 10S, 11R, 11S, 12R, 12S, 13R, 13S and/or 15S position of a fatty acid.

Bioprospecting identified LOX enzymes which act on oleic acid with a 10- or 12-carbon LOX preference. In some embodiments, a lipoxygenase catalyzes hydroperoxidation at the 10-carbon position of a fatty acid. In some embodiments, a lipoxygenase catalyzes hydroperoxidation at the 12-carbon position of a fatty acid. In some embodiments, a LOX catalyzes hydroperoxidation at the 10S and/or 12S-carbon of a fatty acid (i.e., has 10S-LOX or 12S-LOX activity).

In some embodiments, a lipoxygenase has 10S-LOX activity. In some embodiments, a lipoxygenase is a 10S-LOX from a plant, fungus, bacteria, or archaea. In some embodiments, a 10S-LOX facilitates catalysis of oleic acid. In some embodiments, a 10S-LOX is from cyanobacteria. In some embodiments, a 10S-LOX is from cyanobacteria and facilitates catalysis of oleic acid.

A common source of LOX is from plants (for example soybean), with specificity for an unsaturated fatty acid in which LOX activity occurs at the 9- or 13-carbon. In some embodiments, a lipoxygenase is a 9/13-LOX, for example a 9/13-LOX from plants, bacteria, archaea, or fungi.

The following sequences are representative of LOX enzymes that were characterized to have 10S-LOX activity.

In some embodiments, a 10S-LOX is or comprises a sequence any one of SEQ ID NOs: 1 to 12. In some embodiments, a 10S-LOX enzyme has a sequence that is at least about 50% (e.g., at least about 55%, 60%, 65%, 70%, 75%, 80%, 85%, 90%, 95%, 96%, 97%, 98%, 99%, or 100%) identical to any one of SEQ ID NOs: 1 to 12.

```
                                                         (SEQ ID NO: 1)
TRDTSRDGFSNKALAYTLTHFKPIWNLVQSYEPLKRKLNKFFLNSIIYKLPT

RPLPYSLMGLDPKIPGTDIPKKTDTYISWDSLTDKTYTGRHLPPDPEFNKEG

NLPPLDKVKTLFQKRDGKTIYSEKSTLLFPYWVQWFTDSFLRIDQENRFKN

TSNHQIDMCNVYGLTRKQTNMLRAFKDGKFKTQKLKRKDGVEEEYPLFY

YADPEQGIIDPQFEGLHAPLNDEKRQPPEKKSKLFAMGVERANVQIGYVML

NTLCIREHNRICDVLSKSYPEWDDERLFQTARNILMVIVLNIIMEEYIFHITPY

NFRFFADPEAFTKESWYRENWMAIEFSFVYRWHSAIPETFIYDGKEQSMYD

SLWNNQMLIDKGLGALMEETCSQPGTRIGLFNTPDFKIAGTPYTFIDATELA

SVKLGRQAQLASYNDYREMCGYPRVTDFNQITGDEYAQQKLKELYGHVD

KIELFVGLYAEDVRKNSAIPPLVARIIGIDAFSQALTNPLLSPKVFNKETFSEV

GWEIIQNTKTVSDLVNRNVPPSDPKYKVSFEL (SEQ ID NO: 2)
RDTSKDGFRNKLETYALTHFKPIWNLIQSNDTLKKKVNKFLVNNAIYKVPT

RPYPFSTMSPYTSWDSLSDRTYSGLHLPPLDWQPLTNENHLKLKLADTKDF

EKKLPAIEDLRGLYRKSGETKYSPKSTLIFPYFVQWFTDSFLRTDRHNHRKN

TSNHQIDLCTVYGLNAKITHLLRSYQGGKLKSQIINGEEYPPFYYDEKGEAK

KEFIGLPHQLDNDGNPKADTFPLDKKQKLFAMGVEVERSNVQIGYVMLNV

LALREHNRLCELLAKTYPSWDDERLFQTARNILIVEVLRIVVEDYVNHITPY

HFQFITDPLTFSNEKWYRQNWMTVEFTLVYRWHSMLPDTLIYNGQKIPTYE

TQWNNEMIIKQGLGALFEESCSQPCAQLSLFNTPEFLIPVELASVRFGREVK

LRSYNDYRQLCKYPRVTDFDQISSDKNIQKELQRLYGHVDNIELYVGIYAE

DLRENSALPSLVGRLIGIDAFSQVLTNPLLAESVFHPETFSPVGWEEIQNTKT

LSQLLHRNLPPSDKKYRVSFDRAST (SEQ ID NO: 3)
AGKRDTSKDGFDNKVQTFLLTNFKGIWEIVQSNEFLKRKVNKTLINSLIYKI

PTRPNPYSMMTLDEYIPDTKIPKKTDTYTSWELLNDRTYIGRHLPPDPKFNS

EGNLPKVEDLAVLFRKRDGKTIYSPKSTMLFPYWVQWFTDSFLRIDHTKEK

KLKNTSNHEIDLCNVYGLNRKRTHLLRTFKGGKFKTQKLKRQDGIEEEYPL

FYYADPAQGIVDPQFDGLYEPINDEKRLPADKKQYLFAMGVERANVQIGY

VMLNTLCIREHNRLCDELASNYPDWDDERLFQTSRNILMAIILNIIMEEYINH

ITPYHFKLFADPAAFVKESWYRPNWMTIEFDFVYRWHSAIPETFIYDGQPTD

IAASLWNNKMFIDKGLGALMEETCSQPGTRIGLFNTPDILVELTELPSIRLGR
```

-continued

QLQLASYNDYREMCGFPRVTKFEQITGDEFAQEKLKELYGHVDNIEFYVGL

YAEEVRKNSTIPPLVARLIGIDAFSEALNNPLLSPTIFNKDTFSPVGWEIIQNT

KTVSDLINRNVPPSDKKYKVTFDL (SEQ ID NO: 4)
TRDTSRDGFSNKALAYTLTHFKPIWNLVQSYEPLKRKLNKFFLNSIIYKLPT

RPLPYSLMGLDPKIPGTDIPKKTDTYISWDSLTDKTYTGRHLPPDPEFNKEG

NLPPLDKVKTLFQKRDGKTIYSEKSTLLFPYWVQWFTDSFLRIDQENRFKN

TSNHQIDMCNVYGLTRKQTNMLRAFKDGKFKTQKLKRKDGVEEEYPLFY

YADPEQGIIDPQFEGLHAPLNDEKRQPPEKKSKLFAMGVERANVQIGYVML

NTLCIREHNRICDVLSKSYPEWDDERLFQTARNILMVIVLNIIMEEYIFHITPY

NFRFFADPEAFTKESWYRENWMAIEFSFVYRWHSAIPETFIYDGKEQSMYD

SLWNNQMLIDKGLGALMEETCSQPGTRIGLFNTPDFKIAGTPYTFIDATELA

SVKLGRQAQLASYNDYREMCGYPRVTDFNQITGDEYAQQKLKELYGHVD

KIELFVGLYAEDVRKNSAIPPLVARIIGIDAFSQALTNPLLSPKVFNKETFSEV

GWEIIQNTKTVSDLVNRNVPPSDPKYKVSFEE (SEQ ID NO: 5)
RDTSKDGFRNKLETYALTHFKPIWNLIQSNDTLKKKVNKFLVNNAIYKVPT

RPYPFSTMSPYTSWDSLSDRTYSGLHLPPLDWQPLTNENHLKLKLADTKDF

EKKLPAIEDLRGLYRKSGETKYSPKSTLIFPYFVQWFTDSFLRTDRHNHRKN

TSNHQIDLCTVYGLNAKITHLLRSYQGGKLKSQIINGEEYPPFYYDEKGEAK

KEFIGLPHQLDNDGNPKADTFPLDKKQKLFAMGVEVERSNVQIGYVMLNV

LALREHNRLCELLAKTYPSWDDERLFQTARNILIVEVLRIWEDYVNHITPY

HFQFITDPLTFSNEKWYRQNWMTVEFTLVYRWHSMLPDTLIYNGQKIPTYE

TQWNNEMIIKQGLGALFEESCSQPCAQLSLFNTPEFLIPVELASVRFGREVK

LRSYNDYRQLCKYPRVTDFDQISSDKNIQKELQRLYGHVDNIELYVGIYAE

DLRENSALPSLVGRLIGIDAFSQVLTNPLLAESVFHPETFSPVGWEEIQNTKT

LSQLLHRNLPPSDKKYRVSFDRASE (SEQ ID NO: 6)
AGKRDTSKDGFDNKVQTFLLTNFKGIWEIVQSNEFLKRKVNKTLINSLIYKI

PTRPNPYSMMTLDEYIPDTKIPKKTDTYTSWELLNDRTYIGRHLPPDPKFNS

EGNLPKVEDLAVLFRKRDGKTIYSPKSTMLFPYWVQWFTDSFLRIDHTKEK

KLKNTSNHEIDLCNVYGLNRKRTHLLRTFKGGKFKTQKLKRQDGIEEEYPL

FYYADPAQGIVDPQFDGLYEPINDEKRLPADKKQYLFAMGVERANVQIGY

VMLNTLCIREHNRLCDELASNYPDWDDERLFQTSRNILMAIILNIIMEEYINH

ITPYHFKLFADPAAFVKESWYRPNWMTIEFDFVYRWHSAIPETFIYDGQPTD

IAASLWNNKMFIDKGLGALMEETCSQPGTRIGLFNTPDILVELTELPSIRLGR

QLQLASYNDYREMCGFPRVTKFEQITGDEFAQEKLKELYGHVDNIEFYVGL

YAEEVRKNSTIPPLVARLIGIDAFSEALNNPLLSPTIFNKDTFSPVGWEIIQNT

KTVSDLINRNVPPSDKKYKVTFDE (SEQ ID NO: 7)
TRDTSRDGFSNKALAYTLTHFKPIWNLVQSYEPLKRKLNKFFLNSIIYKLPT

RPLPYSLMGLDPKIPGTDIPKKTDTYISWDSLTDKTYTGRHLPPDPEFNKEG

-continued

NLPPLDKVKTLFQKRDGKTIYSEKSTLLFPYWVQWFTDSFLRIDQENRFKN

TSNHQIDMCNVYGLTRKQTNMLRAFKDGKFKTQKLKRKDGVEEEYPLFY

YADPEQGIIDPQFEGLHAPLNDEKRQPPEKKSKLFAMGVERANVQIGYVML

NTLCIREHNRICDVLSKSYPEWDDERLFQTARNILMVIVLNIIMEEYIFHITPY

NFRFFADPEAFTKESWYRENWMAIEFSFVYRWHSAIPETFIYDGKEQSMYD

SLWNNQMLIDKGLGALMEETCSQPGTRIGLFNTPDFKIAGTPYTFIDATELA

SVKLGRQAQLASYNDYREMCGYPRVTDFNQITGDEYAQQKLKELYGHVD

KIELFVGLYAEDVRKNSAIPPLVARIIGIDAFSQALTNPLLSPKVFNKETFSEV

GWEIIQNTKTVSDLVNRNVPPSDPKYKVSFED (SEQ ID NO: 8)
RDTSKDGFRNKLETYALTHFKPIWNLIQSNDTLKKKVNKFLVNNAIYKVPT

RPYPFSTMSPYTSWDSLSDRTYSGLHLPPLDWQPLTNENHLKLKLADTKDF

EKKLPAIEDLRGLYRKSGETKYSPKSTLIFPYFVQWFTDSFLRTDRHNHRKN

TSNHQIDLCTVYGLNAKITHLLRSYQGGKLKSQIINGEEYPPFYYDEKGEAK

KEFIGLPHQLDNDGNPKADTFPLDKKQKLFAMGVEVERSNVQIGYVMLNV

LALREHNRLCELLAKTYPSWDDERLFQTARMLIVEVLRIVVEDYVNHITPY

HFQFITDPLTFSNEKWYRQNWMTVEFTLVYRWHSMLPDTLIYNGQKIPTYE

TQWNNEMIIKQGLGALFEESCSQPCAQLSLFNTPEFLIPVELASVRFGREVK

LRSYNDYRQLCKYPRVTDFDQISSDKNIQKELQRLYGHVDNIELYVGIYAE

DLRENSALPSLVGRLIGIDAFSQVLTNPLLAESVFHPETFSPVGWEEIQNTKT

LSQLLHRNLPPSDKKYRVSFDRASD (SEQ ID NO: 9)
AGKRDTSKDGFDNKVQTFLLTNFKGIWEIVQSNEFLKRKVNKTLINSLIYKI

PTRPNPYSMMTLDEYIPDTKIPKKTDTYTSWELLNDRTYIGRHLPPDPKFNS

EGNLPKVEDLAVLFRKRDGKTIYSPKSTMLFPYWVQWFTDSFLRIDHTKEK

KLKNTSNHEIDLCNVYGLNRKRTHLLRTFKGGKFKTQKLKRQDGIEEEYPL

FYYADPAQGIVDPQFDGLYEPINDEKRLPADKKQYLFAMGVERANVQIGY

VMLNTLCIREHNRLCDELASNYPDWDDERLFQTSRNILMAIILNIIMEEYINH

ITPYHFKLFADPAAFVKESWYRPNWMTIEFDFVYRWHSAIPETFIYDGQPTD

IAASLWNNKMFIDKGLGALMEETCSQPGTRIGLFNTPDILVELTELPSIRLGR

QLQLASYNDYREMCGFPRVTKFEQITGDEFAQEKLKELYGHVDNIEFYVGL

YAEEVRKNSTIPPLVARLIGIDAFSEALNNPLLSPTIFNKDTFSPVGWEIIQNT

KTVSDLINRNVPPSDKKYKVTFDD (SEQ ID NO: 10)
TRDTSRDGFSNKALAYTLTHFKPIWNLVQSYEPLKRKLNKFFLNSIIYKLPT

RPLPYSLMGLDPKIPGTDIPKKTDTYISWDSLTDKTYTGRHLPPDPEFNKEG

NLPPLDKVKTLFQKRDGKTIYSEKSTLLFPYWVQWFTDSFLRIDQENRFKN

TSNHQIDMCNVYGLTRKQTNMLRAFKDGKFKTQKLKRKDGVEEEYPLFY

YADPEQGIIDPQFEGLHAPLNDEKRQPPEKKSKLFAMGVERANVQIGYVML

NTLCIREHNRICDVLSKSYPEWDDERLFQTARNILMVIVLNIIMEEYIFHITPY

NFRFFADPEAFTKESWYRENWMAIEFSFVYRWHSAIPETFIYDGKEQSMYD

SLWNNQMLIDKGLGALMEETCSQPGTRIGLFNTPDFKIAGTPYTFIDATELA

-continued

```
SVKLGRQAQLASYNDYREMCGYPRVTDFNQITGDEYAQQKLKELYGHVD

KIELFVGLYAEDVRKNSAIPPLVARIIGIDAFSQALTNPLLSPKVFNKETFSEV

GWEIIQNTKTVSDLVNRNVPPSDPKYKVSFET
```

```
                                         (SEQ ID NO: 11)
RDTSKDGFRNKLETYALTHFKPIWNLIQSNDTLKKKVNKFLVNNAIYKVPT

RPYPFSTMSPYTSWDSLSDRTYSGLHLPPLDWQPLTNENHLKLKLADTKDF

EKKLPAIEDLRGLYRKSGETKYSPKSTLIFPYFVQWFTDSFLRTDRHNHRKN

TSNHQIDLCTVYGLNAKITHLLRSYQGGKLKSQIINGEEYPPFYYDEKGEAK

KEFIGLPHQLDNDGNPKADTFPLDKKQKLFAMGVEVERSNVQIGYVMLNV

LALREHNRLCELLAKTYPSWDDERLFQTARNILIVEVLRIVVEDYVNHITPY

HFQFITDPLTFSNEKWYRQNWMTVEFTLVYRWHSMLPDTLIYNGQKIPTYE

TQWNNEMIIKQGLGALFEESCSQPCAQLSLFNTPEFLIPVELASVRFGREVK

LRSYNDYRQLCKYPRVTDFDQISSDKNIQKELQRLYGHVDNIELYVGIYAE

DLRENSALPSLVGRLIGIDAFSQVLTNPLLAESVFHPETFSPVGWEEIQNTKT

LSQLLHRNLPPSDKKYRVSFDRASL
```

```
                                         (SEQ ID NO: 12)
AGKRDTSKDGFDNKVQTFLLTNFKGIWEIVQSNEFLKRKVNKTLINSLIYKIPTR

PNPYSMMTLDEYIPDTKIPKKTDTYTSWELLNDRTYIGRHLPPDPKFNSEGNLPKVEDLA

VLFRKRDGKTIYSPKSTMLFPYWVQWFTDSFLRIDHTKEKKLKNTSNHEIDLCNVYGLN

RKRTHLLRTFKGGKFKTQKLKRQDGIEEEYPLFYYADPAQGIVDPQFDGLYEPINDEKRL

PADKKQYLFAMGVERANVQIGYVMLNTLCIREHNRLCDELASNYPDWDDERLFQTSRN

ILMAIILNIIMEEYINHITPYHFKLFADPAAFVKESWYRPNWMTIEFDFVYRWHSAIPETFI

YDGQPTDIAASLWNNKMFIDKGLGALMEETCSQPGTRIGLFNTPDILVELTELPSIRLGR

QLQLASYNDYREMCGFPRVTKFEQITGDEFAQEKLKELYGHVDNIEFYVGLYAEEVRK

NSTIPPLVARLIGIDAFSEALNNPLLSPTIFNKDTFSPVGWEIIQNTKTVSDLINRNVPPSDK

KYKVTFDT
```

Also provided are herein are circular permutated variants of any enzyme or polypeptide described herein. In circular permutation methods, the N- and C-terminus of the mutated protein are redefined by genetic engineering. Circular permutation methods have been described in the art. For example, Graf and Schachmann, (Proc. Natl. Acad. Sci. USA (1996) 93, 11591-11596), provide an overview of enzymes and other proteins with which circular permutation methods have been carried out. Methods for engineering circular permutated polypeptide (e.g., enzyme) variants are known in the art, see, e.g., US Pat. Publ. No. 2010/0196991. In some embodiments, a circular permutation variant includes a linker.

In some embodiments, an enzyme for use in the context of the present disclosure is a cyanobacterial enzyme with LOX activity (e.g., 10S-LOX activity) or variant thereof. In some embodiments, a cyanobacterial prostaglandin-endoperoxide synthase enzyme or variant thereof has LOX activity (e.g., 10S-LOX activity). In some embodiments, an enzyme with LOX catalytic activity (e.g., 10S-LOX activity) comprises an amino acid sequence of SEQ ID NO: 13 and/or a circular permutation thereof.

```
                                         (SEQ ID NO: 13)
TRDTSRDGFSNKALAYTLTHFKPIWNLVQSYEPLKRKLNKFFLNSIIY

KLPTRPLPYSLMGLDPKIPGTDIPKKTDTYISWDSLTDKTYTGRHLPP

DPEFNKEGNLPPLDKVKTLFQKRDGKTIYSEKSTLLFPYWVQWFTDSF

LRIDQENRFKNTSNHQIDMCNVYGLTRKQTNMLRAFKDGKFKTQKLKR

KDGVEEEYPLFYYADPEQGIIDPQFEGLHAPLNDEKRQPPEKKSKLFA

MGVERANVQIGYVMLNTLCIREHNRICDVLSKSYPEWDDERLFQTARN

ILMVIVLNIIMEEYIFHITPYNFRFFADPEAFTKESWYRENWMAIEFS
```

-continued

FVYRWHSAIPETFIYDGKEQSMYDSLWNNQMLIDKGLGALMEETCSQP

GTRIGLFNTPDFKIAGTPYTFIDATELASVKLGRQAQLASYNDYREMC

GYPRVTDFNQITGDEYAQQKLKELYGHVDKIELFVGLYAEDVRKNSAI

PPLVARIIGIDAFSQALTNPLLSPKVFNKETFSEVGWEIIQNTKTVSD

LVNRNVPPSDPKYKVSFEX, where X is any amino acid.

In some embodiments, a cyanobacterial heme peroxide synthase enzyme or variant thereof has LOX activity (e.g., 10S-LOX activity). In some embodiments, an enzyme with LOX (e.g., 10S-LOX activity) catalytic activity comprises an amino acid sequence of SEQ ID NO: 14 and/or a circular permutation thereof. In some embodiments, an enzyme with LOX (e.g., 10S-LOX activity) catalytic activity comprises an amino acid sequence of SEQ ID NO: 15 and/or a circular permutation thereof.

(SEQ ID NO: 14)
RDTSKDGFRNKLETYALTHFKPIWNLIQSNDTLKKKVNKFLVNNAIYK

VPTRPYPFSTMSPYTSWDSLSDRTYSGLHLPPLDWQPLTNENHLKLKL

ADTKDFEKKLPAIEDLRGLYRKSGETKYSPKSTLIFPYFVQWFTDSFL

RTDRHNHRKNTSNHQIDLCTVYGLNAKITHLLRSYQGGKLKSQIINGE

EYPPFYYDEKGEAKKEFIGLPHQLDNDGNPKADTFPLDKKQKLFAMGV

EVERSNVQIGYVMLNVLALREHNRLCELLAKTYPSWDDERLFQTARNI

LIVEVLRIVVEDYVNHITPYHFQFITDPLTFSNEKWYRQNWMTVEFTL

VYRWHSMLPDTLIYNGQKIPTYETQWNNEMIIKQGLGALFEESCSQPC

AQLSLFNTPEFLIPVELASVRFGREVKLRSYNDYRQLCKYPRVTDFDQ

ISSDKNIQKELQRLYGHVDNIELYVGIYAEDLRENSALPSLVGRLIGI

DAFSQVLTNPLLAESVFHPETFSPVGWEEIQNTKTLSQLLHRNLPPSD

KKYRVSFDRASX, where X is any amino acid.

(SEQ ID NO: 15)
AGKRDTSKDGFDNKVQTFLLTNFKGIWEIVQSNEFLKRKVNKTLINSL

IYKIPTRPNPYSMMTLDEYIPDTKIPKKTDTYTSWELLNDRTYIGRHL

PPDPKFNSEGNLPKVEDLAVLFRKRDGKTIYSPKSTMLFPYWVQWFTD

SFLRIDHTKEKKLKNTSNHEIDLCNVYGLNRKRTHLLRTFKGGKFKTQ

KLKRQDGIEEEYPLFYYADPAQGIVDPQFDGLYEPINDEKRLPADKKQ

YLFAMGVERANVQIGYYMLNTLCIREHNRLCDELASNYPDWDDERLFQ

TSRNILMAIILNIIMEEYINHITPYHFKLFADPAAFVKESWYRPNWMT

IEFDFVYRWHSAIPETFIYDGQPTDIAASLWNNKMFIDKGLGALMEET

CSQPGTRIGLFNTPDILVELTELPSIRLGRQLQLASYNDYREMCGFPR

VTKFEQITGDEFAQEKLKELYGHVDNIEFYVGLYAEEVRKNSTIPPLV

ARLIGIDAFSEALNNPLLSPTIFNKDTFSPVGWEIIQNTKTVSDLINR

NVPPSDKKYKVTFDLX, where X is any amino acid.

Figure 5:
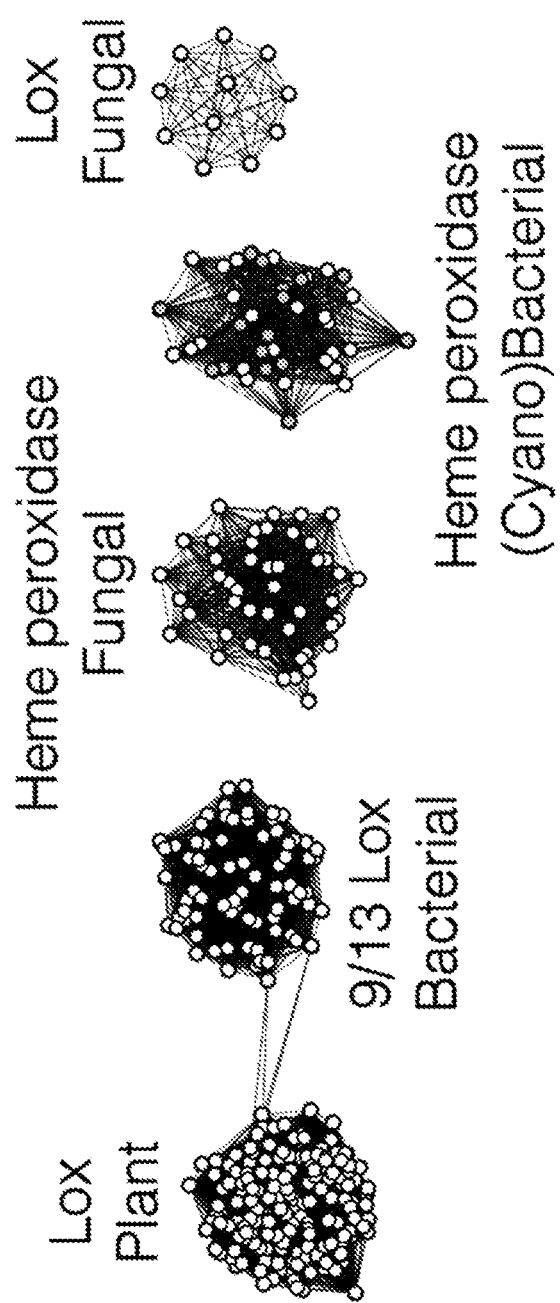
FIG. 5 is a schematic illustrating relatedness of certain enzymes for 10S-LOX activity.

A sequence similarity network of LOX enzymes is tested for activity on oleic acid and depicted in FIG. 5. Gray nodes indicate 10S-LOX activity. These sequences are distinct from 9/13-LOX from plants, bacteria, and fungi, and are sometimes annotated as heme peroxidases. In particular, the cluster contains primarily cyanobacterial enzymes contains the 10S-LOXs that are active on oleic acid.

In some embodiments, a fatty acid to be degraded is oleic acid, and a LOX enzyme specific for action on the 10S- or 12S-carbon of oleic acid is employed in a composition or method of the present disclosure.

Dioxygenases and Monooxygenases

In some embodiments, dioxygenases other than LOX, as well as monooxygenases, are suitable for use in the context of the present disclosure. In some embodiments, an enzyme is a dioxygenase. In some embodiments, an enzyme is a monooxygenase.

In some embodiments, a dioxygenase catalyzes oxidation of a fatty acid substrate. In some embodiments, a fatty acid substrate is an unsaturated fatty acid. In some embodiments, a dioxygenase catalyzes oxidation of palmitoleic acid, oleic acid, myristoleic acid, linoleic acid, and/or arachidonic acid.

In some embodiments, a dioxygenase catalyzes the partial or complete degradation of one or more unsaturated fatty acids. In some embodiments, a dioxygenase facilitates partial or complete degradation of palmitoleic acid, oleic acid, myristoleic acid, linoleic acid, and/or arachidonic acid.

In some embodiments, a monooxygenase catalyzes oxidation of a fatty acid substrate. In some embodiments, a fatty acid substrate is an unsaturated fatty acid. In some embodiments, a monooxygenase catalyzes oxidation of palmitoleic acid, oleic acid, myristoleic acid, linoleic acid, and/or arachidonic acid.

In some embodiments, a monooxygenase catalyzes the partial or complete degradation of one or more unsaturated fatty acids. In some embodiments, a monooxygenase facilitates partial or complete degradation palmitoleic acid, oleic acid, myristoleic acid, linoleic acid, and/or arachidonic acid.

In some embodiments, a dioxygenase and/or a monooxygenase is from a plant, bacteria, archaea, or fungus. In some embodiments, a dioxygenase and/or a monooxygenase facilitates catalysis of oleic acid. In some embodiments, a dioxygenase and/or a monooxygenase is from cyanobacteria. In some embodiments, a dioxygenase and/or a monooxygenase is from cyanobacteria and facilitates catalysis of oleic acid.

In some embodiments, an enzyme catalyzes beta or omega oxidation. In some embodiments, an enzyme catalyzes oxidation or hydroperoxidation at the 5, 8, 9, 10, 11, 12, 13 or 15-carbon of a fatty acid. In some embodiments, an enzyme catalyzes oxidation or hydroperoxidation at a 5R, 5S, 8R, 8S, 9R, 9S, 10S, 11R, 11S, 12R, 12S, 13R, 13S and/or 15S position of a fatty acid. In some embodiments, an enzyme catalyzes oxidation or hydroperoxidation of the 10S and/or 12S-carbon of a fatty acid (e.g., an oleic acid). In some embodiments, an enzyme for use in the context of the present disclosure does not require adenosine triphosphate (ATP) for catalytic activity.

In some embodiments, a monooxygenase and/or dioxygenase in the context of the present disclosure can catalyze partial or complete degradation of a fatty acid (e.g., an unsaturated fatty acid). In some embodiments, activity of a monooxygenase and/or dioxygenase may be independent of cofactors (e.g., ATP). In some embodiments, activity of a monooxygenase and/or dioxygenase may require a cofactor (e.g., ATP).

In some embodiments, compositions and methods of the present disclosure comprise a LOX and one or more other dioxygenases that promote breakdown of compounds that cause damage to polymers. In some embodiments, compositions and methods of the present disclosure comprise a LOX and one or more monooxygenases that promote breakdown of compounds that cause damage to polymers. In some embodiments, compositions and methods of the present disclosure comprise a plurality of enzymes. In some embodiments, each of the enzymes can degrade an unsaturated fatty acid. In some embodiments, each of the plurality of enzymes exhibit different substrate specificity for one or more unsaturated fatty acids.

P450s

In some embodiments, an enzyme suitable for use in the context of the present disclosure is a P450. Cytochrome P450 enzymes form a superfamily of hemoproteins found in bacteria, archaea and eukaryotes. In a common activity, cytochrome P450 acts as a monooxygenase, by inserting one oxygen atom of molecular oxygen into a substrate molecule, while the other oxygen atom is reduced to water. A P450 catalytic reaction may require two electrons for the activation of molecular oxygen. P450s from eukaryotes use NADPH as the external reductant and source of electrons. Each electron may be transferred one at a time to a cytochrome P450 active site. In some embodiments, an electron transfer may be donated by an electron donor protein, e.g., a cytochrome P450 reductase (CPR). A CPR may be an electron donor protein for several different P450s from the same or from different organisms. In some cases P450s can also be coupled to a cytochrome b5 protein that can act as the electron donor protein or can improve the efficiency of the electron transfer from the CPR to the P450. In eukaryotic cells and particularly in plants, P450s and CPRs are generally membrane-bound proteins and are associated with the endoplasmic reticulum. These proteins may be anchored to the membrane by an N-terminal transmembrane helix.

Many P450s have low substrate specificity and are therefore able to catalyze the oxidation of many diverse structures. Many P450s have a particular region and stereoselectivity with a given substrate; however they produce a mixture of several products from a particular substrate. In some embodiments, a P450 is involved in breakdown and detoxification of molecules (e.g., xenobiotics). In some embodiments, a P450 is involved in a biosynthetic pathway. P450s involved in a biosynthetic pathway may exhibit specificity for certain types of substrates and region and stereo-selectivity. In some embodiments, a P450 is from a plant, bacteria, or fungus.

A large number of P450s can be found in nature and particularly in plants. One plant genome can contain several hundreds of genes encoding for P450s.

In some embodiments, a P450 is active on one or more unsaturated fatty acids. In some embodiments, a P450 facilitates catalysis of palmitoleic acid, oleic acid, myristoleic acid, linoleic acid, and/or arachidonic acid. In some embodiments, a P450 facilitates catalysis of oleic acid.

In some embodiments, compositions and methods of the present disclosure comprise a P450 and another enzyme (e.g., a dioxygenase, monooxygenase, heme peroxidase) that promote breakdown of compounds that cause damage. In some embodiments, compositions and methods of the present disclosure comprise a plurality of enzymes. In some embodiments, each of the enzymes can act on an unsaturated fatty acid. In some embodiments, each of the enzymes can degrade an unsaturated fatty acid. In some embodiments, each of the plurality of enzymes exhibit different substrate specificity for one or more unsaturated fatty acids.

Heme Peroxidases

In some embodiments, an enzyme for use in the context of the present disclosure is a heme peroxidase. In some embodiments, a heme peroxidase has a ferriprotoporphyrin IX prosthetic group located at the active site. The plant enzymes horseradish peroxidase (HRP) and plant soyabean peroxidase (SBP) are examples of plant heme peroxidases.

In some embodiments, a heme peroxidase facilitates catalysis of one or more unsaturated fatty acids. In some embodiments, a heme peroxidase facilitates catalysis of palmitoleic acid, oleic acid, myristoleic acid, linoleic acid, and/or arachidonic acid. In some embodiments, a heme peroxidase facilitates catalysis of oleic acid.

In some embodiments, compositions and methods of the present disclosure comprise a heme peroxidase and another enzyme (e.g., a dioxygenase, monooxygenase, P450) that promotes breakdown of compounds that cause damage to polymers. In some embodiments, compositions and methods of the present disclosure comprise a plurality of enzymes. In some embodiments, each of the enzymes facilitates catalysis of an unsaturated fatty acid. In some embodiments, each of the enzymes can degrade an unsaturated fatty acid. In some embodiments, each of the plurality of enzymes exhibit different substrate specificity for one or more unsaturated fatty acids.

Polypeptides

In some embodiments, protection of materials from damaging lipids (e.g., fatty acids, such as oleic acid and other unsaturated fatty acids), is additionally or alternatively performed via non-catalytic binding of a protein to a lipid. In some embodiments, binding to a lipid (e.g., an unsaturated fatty acid) results in formation of a protein-lipid complex that would be less able to diffuse into the material being protected. Binding of a lipid (e.g., an unsaturated fatty acid) could also limit or prevent it from reacting with other materials, such as a polymeric material or other material to be protected.

In some embodiments, compositions are provided comprising one or more enzymes that promote breakdown of a fatty acid and one or more polypeptides that form a complex with a fatty acid.

Nucleic Acid Construction and Expression

Enzymes and polypeptides as described herein may be produced from nucleic acid molecules using molecular biological methods known to the art. Nucleic acid molecules are inserted into a vector that is able to express the polypeptide when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the enzymes of the present disclosure under control of transcriptional/translational control signals. These methods may include in vitro recombinant DNA and synthetic techniques and in vivo recombination (See Sambrook et al., Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present disclosure may be regulated by a second nucleic acid sequence so that the molecule is expressed in a host transformed with the recombinant DNA molecule. For example, expression of the nucleic acid molecules of the present disclosure may be controlled by promoter and/or enhancer elements, which are known in the art.

Nucleic acid constructs of the present disclosure may be inserted into an expression vector or viral vector by methods known to the art, and nucleic acid molecules operatively linked to an expression control sequence.

Where appropriate, nucleic acid sequences that encode enzyme as described herein may be modified to include codons that are optimized for expression in a particular cell type or organism. Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for an enzyme as described herein may be optimized for expression in bacterial cells, fungal cells, plant cells, mammalian cells, etc. Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., yeast cells or mammalian cells). Host cells transformed with an expression vector are grown under conditions permitting production of an enzyme of the present disclosure followed by recovery of the enzyme or polypeptide.

Enzyme and polypeptides of the present disclosure may be purified by any technique, which allows for the subsequent formation of a stable enzyme. For example, not wishing to be bound by theory, enzymes may be recovered from cells either as soluble polypeptides or as inclusion bodies, from which they may be extracted quantitatively by 8M guanidinium hydrochloride and dialysis. In order to further purify enzymes of the present disclosure, conventional ion exchange chromatography, hydrophobic interaction chromatography, reverse phase chromatography or gel filtration may be used. Enzymes of the present invention may also be recovered from conditioned media following secretion from eukaryotic or prokaryotic cells.

Polymers

Biological fluids may include components that can damage polymers. For example, fatty acids (e.g., unsaturated fatty acids or other fatty acids) may include reactive compounds such as peroxide that can damage polymers. The present invention encompasses the recognition that protective enzymes may be incorporated into a polymer to prevent, mitigate or lessen damage to a polymer and/or a device containing the polymer. The protective enzymes may include any enzymes described herein suitable to protect against biological substances (e.g., fatty acids) that may degrade or otherwise damage polymeric materials.

In some embodiments, polymers suitable for use in the context of the present disclosure may include polyamides, polyesters, polyaryletherketones, polyimides, polyetherimides, polyamideimide, liquid crystalline polymers, polycarbonates, polyolefins, polyphenylene oxide, polysulfones, polyacrylates, acrylonitrile butadiene styrene polymer, polyoxymethylene, polystyrene, polyarylene sulfide, polyvinylidene fluoride, polytetrafluoroethylene, polyvinylidene chloride, polyvinyl chloride, and any other suitable polymer. In some embodiments, a polymer is or comprises a silicone resin, epoxy resin, polyvinyl butyral resin, cellulose acetate, ethylene-vinyl acetate copolymer (EVA) or an ionomer. In some embodiments, a polymer is or comprises an acrylic-based polymer. In some embodiments, a polymer is or comprises a silicon-based polymer.

In some embodiments, a protective enzyme or polypeptide is embedded within a polymeric composition. In some embodiments, a polymeric composition comprises a protective enzyme or polypeptide within a range from about 0.0001% to about 20% on w/w basis. In some embodiments, a polymeric composition comprises two or more protective enzymes, each present within a range from about 0.0001% to about 20% on w/w basis. In some embodiments, a polymeric composition comprises a protective enzyme or polypeptide within a range bounded by a lower limit and an upper limit, the upper limit being larger than the lower limit. In some embodiments, the lower limit may be about 0.0001%, 0.0002%, 0.0005%, 0.001%, 0.002%, 0.005%, 0.01%, 0.02%, 0.05%, 0.1%, 0.2%, 0.5%, 1%, 2%, 5%, or 10%. In some embodiments, the upper limit may be about 0.0005%, 0.001%, 0.002%, 0.005%, 0.01%, 0.02%, 0.05%, 0.1%, 0.2%, 0.5%, 1%, 2%, 5%, 10%, or 20%.

In some embodiments, a protective enzyme is applied to the surface of a polymeric composition. In some embodiments, a polymeric composition is coated with a protective enzyme.

Components of Electronic Devices

Electronic devices may be exposed to the bodily fluids of users such as sweat and sebum. These bodily fluids may contain fatty acids that degrade polymers in electronic devices. To prevent degradation, protective enzymes may be incorporated into one or more components of electronic device. Protective enzymes may include, for example, one or more enzymes from the lipoxygenase (LOX) enzyme family, or other suitable enzymes that degrade harmful substances such as fatty acids. Protective enzymes such as lipoxygenase enzymes can degrade these reactive compounds (e.g., peroxide) and thereby reduce the ability of a fatty acid (e.g., oleic acid, etc.) to degrade polymers and damage electronic devices. Protective enzymes may neutralize the destructive activity of the fatty acids and thereby help enhance robustness of polymer structures for electronic devices.

In some embodiments, a polymer with a protective enzyme may be part of an adhesive, gasket, tape, button, or other structure that may be vulnerable to damage by exposure to biological lipids (e.g., fatty acids). A protective enzyme may be incorporated into a coating, an adhesive, a gasket, or other structures in an electronic device. When fatty acids come into contact with a protective enzyme in a coating, adhesive, gasket, or other structure, the fatty acids in the structures are neutralized.

In general, any suitable components in an electronic device may include one or more protective enzymes (e.g., dioxygenases, monooxygenases, heme peroxidases, P450s, and/or lipoxygenases). For example, a protective enzyme may be incorporated into plastic portions of housings, gaskets, adhesive layers, tape layers, coatings, gap filling sealant and other sealants, liquid polymers that are dispensed as coatings, room temperature adhesives, fluoropolymer coatings and/or other hydrophobic coatings, liquid polymer materials that serve as carrier fluids for enzyme dispensing without serving as structural adhesive, and/or other materials (e.g., polymers) in an electronic device.

Topical Formulations

In some embodiments, a protective enzyme and/or polypeptide may be used as part of a topical formulation for application to the skin of a mammal (e.g., a human). In some embodiments, a protective enzyme and/or polypeptide may be used as part of a topical formulation for application to a polymer. In some embodiments, the polymer is a component of a device. In some embodiments, a protective enzyme and/or polypeptide may be used as part of a topical formulation for application to a device that comprises a polymer. Without wishing to be bound by theory, it is envisioned that inclusion of a protective enzyme and/or polypeptide may prevent degradation of other components of a topical formulation. In some embodiments, two or more protective enzymes may be used a part of a topical formulation for application to the skin of a mammal (e.g., a human). In some embodiments a mixture of enzymes may be used as part of a topical formulation. For example, it may be desirable to combine enzymes with specificities to multiple unsaturated fatty acids, for example to both oleic and linoleic acid present in sebum and sweat. Similarly, single enzymes or mixtures could be employed to target oleic acid or multiple unsaturated fatty acids in products applied to the skin.

In some embodiments, a topical formulation comprising a protective enzyme and/or polypeptide is an emulsion, gel, ointment, or lotion. Topical formulations may be prepared using methods known in the art, for example, as provided by reference texts such as, REMINGTON: THE SCIENCE AND PRACTICE OF PHARMACY 1577-1591, 1672-1673, 866-885; (Alfonso R. Gennaro ed. 19th ed. 1995); Ghosh, T. K.; et al. TRANSDERMAL AND TOPICAL DRUG DELIVERY SYSTEMS (1997), both of which are hereby incorporated herein by reference.

In some embodiments, a protective enzyme and/or polypeptide may be useful for compositions comprising a medicament for topical formulation. In some embodiments, a protective enzyme and/or polypeptide is a component of a topical sunscreen formulation.

In some embodiments, a topical formulation comprises a protective enzyme or polypeptide within a range from about 0.0001% to about 20% on w/w basis. In some embodiments, a polymeric composition comprises two or more protective enzymes, each present within a range from about 0.0001% to about 20% on w/w basis. In some embodiments, a topical formulation comprises a protective enzyme or polypeptide within a range bounded by a lower limit and an upper limit, the upper limit being larger than the lower limit. In some embodiments, the lower limit may be about 0.0001%, 0.0002%, 0.0005%, 0.001%, 0.002%, 0.005%, 0.01%, 0.02%, 0.05%, 0.1%, 0.2%, 0.5%, 1%, 2%, 5%, or 10%. In some embodiments, the upper limit may be about 0.0005%, 0.001%, 0.002%, 0.005%, 0.01%, 0.02%, 0.05%, 0.1%, 0.2%, 0.5%, 1%, 2%, 5%, 10%, or 20%.

The foregoing is merely illustrative and various modifications can be made to the described embodiments. The foregoing embodiments may be implemented individually or in any combination.

EXAMPLES

Example 1

An Exemplary Protective Enzyme Prevents Fatty Acid Induced Polymer Swelling

Figure 2:
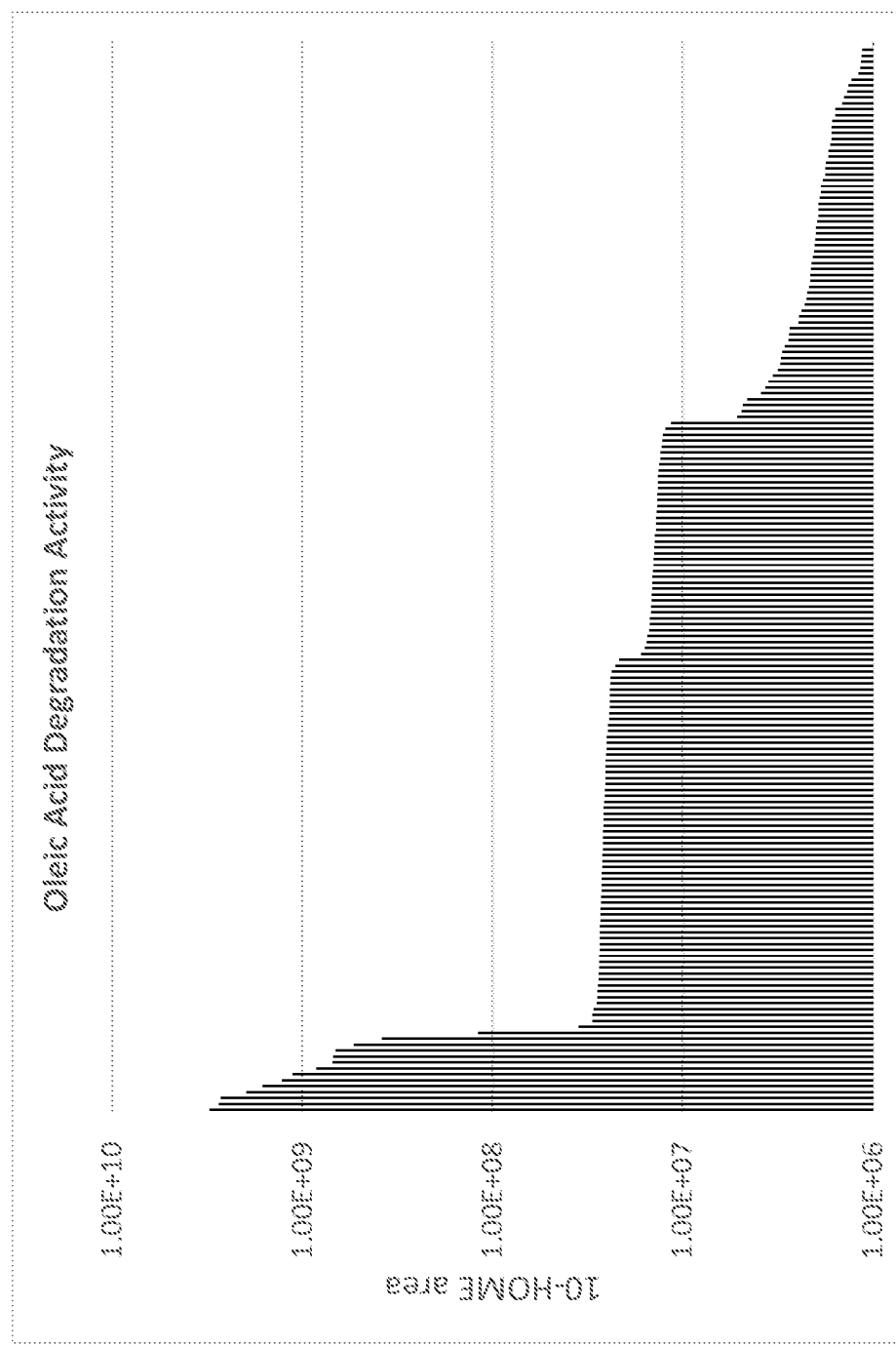
FIG. 2 depicts enzyme activity data generated by assaying various LOX enzymes for activity on oleic acid and detecting the 10-HOME product shown in FIG. 1.

This example shows the enzymatic activity of a series of LOX enzymes that were assayed for activity on oleic acid. The chemical activity of the enzymes that is measured is shown in FIG. 1. The assay detects the 10-HOME product derived from treatment of the unstable peroxide produced by the LOX enzyme with the reducing agent DTT. Enzymes were tested in the context of *E. coli* cell lysate. *E. coli* overexpressing the LOX enzyme were induced, then cells were lysed enzymatically using lysozyme. The lysate was added to the reaction containing oleic acid, dodecyl maltoside as a surfactant and Tris buffer pH7.6 and the reaction was run at room temperature for 15 minutes. The reaction product was reduced using DTT and quenched in a methanol/acetonitrile mixture, and 10-HOME product was quantified using LC-MS. Resulting activity is shown in FIG. 2.

Example 2

An Exemplary Protective Enzyme Prevents Fatty Acid Induced Polymer Swelling

Figure 3:
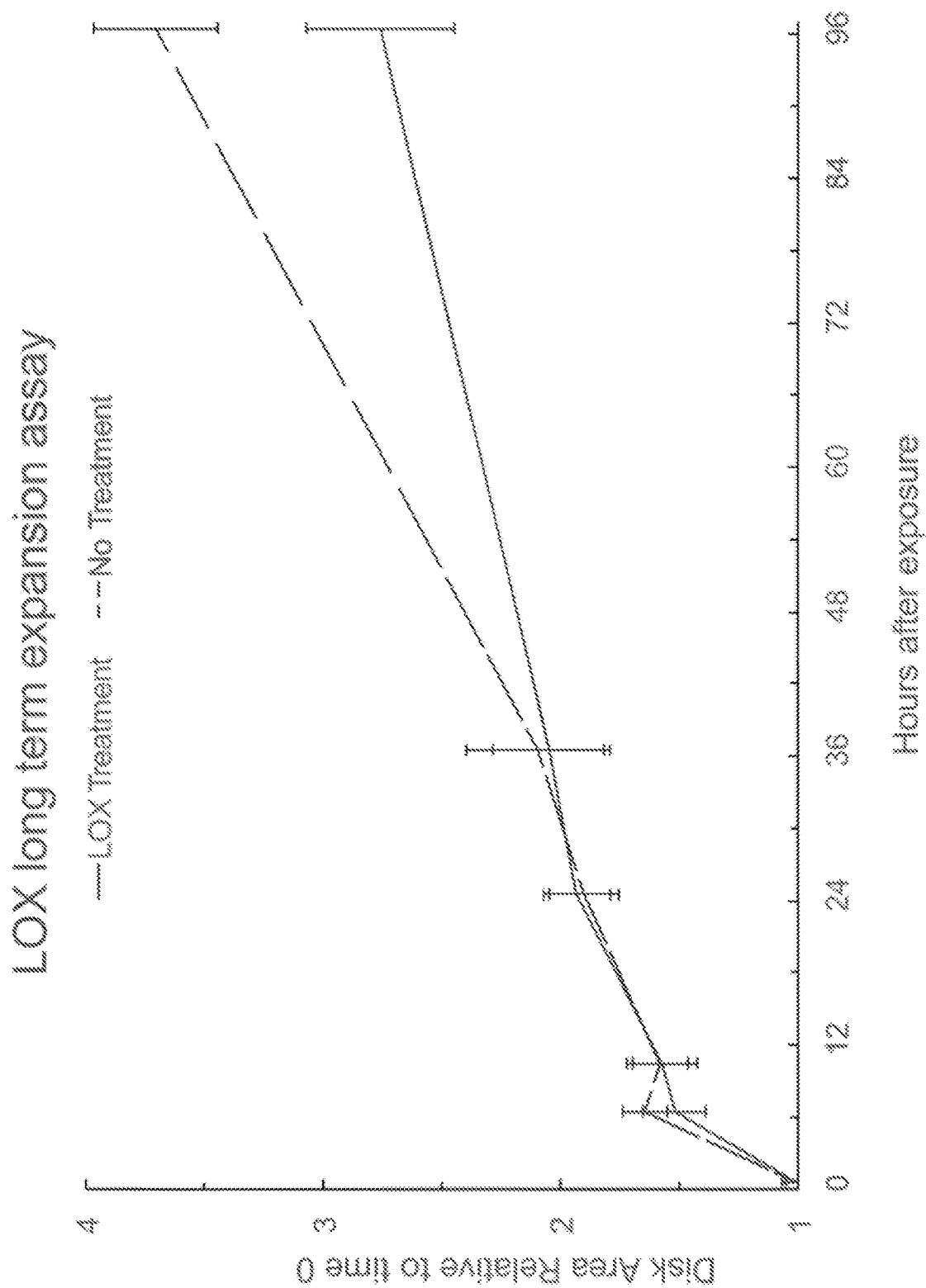
FIG. 3 depicts swelling of a representative adhesive upon exposure to an exemplary fatty acid, oleic acid. X-axis indicates the number of hours post-exposure; Y-axis indicates the relative area of an adhesive disk.

This example demonstrates the efficacy of an exemplary protective enzyme (e.g., a lipoxygenase). Specifically, this Example demonstrates that a polymer composition comprising an exemplary protective enzyme (e.g., a lipoxygenase) is able to prevent polymer swelling induced by treatment with a fatty acid. An acrylic foam pressure sensitive adhesive tape (3M™ VHB™ Tape 4914-015) was used as a representative composition to assess the efficacy protective enzymes to prevent polymeric swelling. This representative adhesive was exposed to an exemplary unsaturated fatty acid (oleic acid), and polymer swelling was assessed over time for both lipoxygenase treated (treated) and untreated samples, FIG. 3. Y-axis indicates the amount of swelling by area, X-axis indicates the number of hours post-exposure. As can be seen in FIG. 3, beginning at approximately 40 hours, the untreated samples show an increase in swelling greater than that of the treated samples. Thus, treatment with a lipoxygenase protected the representative adhesive from fatty acid induced damage over time.

Example 3

An Exemplary of an Alternative Assay Demonstrating Protective Enzyme Efficacy

Figure 4:
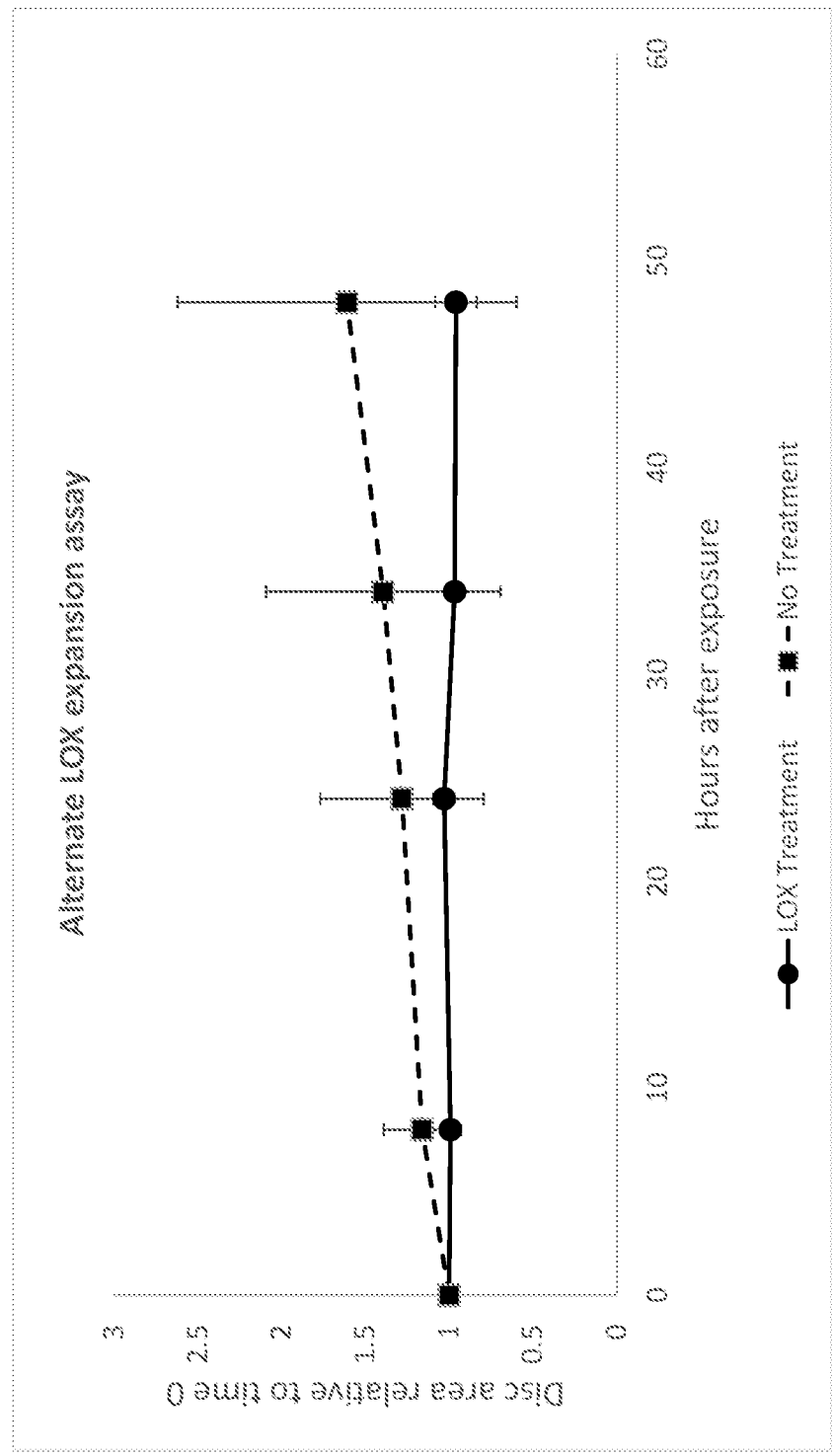
FIG. 4 depicts swelling of a representative adhesive upon exposure to an exemplary fatty acid, oleic acid, using a second assay. X-axis indicates the number of hours post-exposure; Y-axis indicates the relative area of an adhesive disk.

This example provides additional evidence of the protective effect of a protective enzyme on the swelling induced in an adhesive by fatty acids. An acrylic foam pressure sensitive adhesive tape (3M™ VHB™ Tape 4914-015) was used as a representative composition to assess the efficacy protective enzymes to prevent polymeric swelling. This representative adhesive was first treated with either lipoxygenase or left untreated and then exposed to an exemplary unsaturated fatty acid (oleic acid). Polymer swelling was assessed over time for both lipoxygenase treated (treated) and untreated samples, FIG. 4. Y-axis indicates the amount of swelling by area, X-axis indicates the number of hours post-exposure. As can be seen in FIG. 4, the untreated samples show an increase in swelling greater than that of the treated samples. Thus, pre-treatment with a lipoxygenase protected the representative adhesive from fatty acid induced damage over time.

Example 4

Analysis of LOX Family Enzymes for Activity

This example describes assessment of a network of LOX enzymes for catalytic activity on an exemplary fatty acid substrate (e.g., oleic acid). Homologs of extant lipoxygenases were identified via bioinformatics methods, based on sequence and structural similarity. Each node represents a candidate LOX enzyme, with each enzyme clustered by pairwise similarity to the other enzymes in the library. Gray nodes were shown to have 10S-LOX activity on oleic acid. These 10S-LOX enzymes are distantly related to the more well-described 9S/13S-LOX enzymes described for plants and bacteria. The above example demonstrates that lipoxygenases are a class of enzyme that can degrade an exemplary fatty acid, oleic acid. Moreover, it is determined that other enzymes, such as dioxygenases, monooxygenases, heme peroxidases, P450s, and others could also catalyze the degradation of lipids such as fatty acids.

Enzyme family networks are depicted in FIG. 5, with gray nodes indicating possession 10S-LOX activity. Thus, several different heme peroxidase enzymes possess 10S-LOX activity. These sequences are distinct from 9/13-LOX from plants, bacteria, and fungi. Of note, the cluster contains primarily cyanobacterial enzymes was found to contain 10S-LOXs that are active on the specific exemplary fatty acid (oleic acid). The assays described herein can be used to characterize the ability of enzymes to protect from damage induced by lipids (e.g., specific fatty acids and/or combinations of fatty acids).

EXEMPLARY EMBODIMENTS

1. A method for promoting the breakdown of one or more fatty acids in bodily fluid secreted from a human, the method comprising contacting the bodily fluid with an enzyme.

2. A method for inhibiting swelling of a polymer caused by exposure to a fatty acid, the method comprising contacting the polymer with an enzyme.

3. A method for inhibiting swelling of a polymer caused by exposure to a fatty acid, the method comprising contacting the polymer with a polypeptide that binds a fatty acid.

4. The method according to any one of embodiments 1-3 wherein the fatty acid is unsaturated.

5. The method according to any one of embodiments 1-3 wherein the fatty acid is an oleic acid.

6. The method according to any one of embodiments 1-3 wherein the fatty acid is a linoleic acid.

7. The method according to any one of embodiments 1-6 wherein the enzyme or polypeptide is embedded in a polymer.

8. The method according to any one of embodiments 1 or 4-7 wherein the bodily fluid comprises sweat.

9. The method according to any one of embodiments 1 or 4-7 wherein the bodily fluid comprises sebum.

10. The method according to any one of embodiments 1-2, or 4-9 wherein the enzyme is a dioxygenase.

11. The method according to any one of embodiments 1-2, or 4-9 wherein the enzyme is a lipoxygenase.

12. The method according to any one of embodiments 1-2, or 4-9 wherein the enzyme is a monooxygenase.

13. The method according to any one of embodiments 1-2, or 4-9 wherein the enzyme does not require adenosine triphosphate (ATP) for catalytic activity.

14. The method according to any one of embodiments 1-2, or 4-13 comprising contacting the bodily fluid or polymer with a plurality of enzymes.

15. The method according to embodiment 14, wherein the plurality of enzymes comprises a dioxygenase, monooxygenase, heme peroxidases, and/or P450s.

16. The method according to any one of embodiments 1-2, or 4-15 wherein the enzyme is a cyanobacterial enzyme.

17. The method according to any one of embodiments 1-2, or 14-16 wherein the enzyme catalyzes beta or omega oxidation.

18. The method according to any one of embodiments 1-2, or 14-17 wherein the enzyme has activity at the 10S and/or 12S-carbon of an oleic acid.

19. The method according to embodiment 3 wherein the polypeptide forms a complex with the fatty acid.

20. The method according to embodiment 3 wherein the polypeptide inhibits reactivity of the fatty acid.

21. The method according to embodiment 3 wherein the polypeptide inhibits diffusion of the fatty acid.

22. A composition comprising a polymer and one or more enzymes that promote breakdown of a fatty acid.

23. A composition comprising a polymer and one or more polypeptides that bind to a fatty acid.

24. The composition according to embodiment 22 or 23 wherein the one or more enzymes or polypeptides are embedded in the polymer.

25. The composition according to any one of embodiments 22-24 wherein the fatty acid is unsaturated.

26. The composition according to any one of embodiments 22-24 wherein the fatty acid is an oleic acid.

27. The composition according to any one of embodiments 24-24 wherein the fatty acid is a linoleic acid.

28. The composition according to any one of embodiments 22, or 24-27 wherein the enzyme is a dioxygenase.

29. The composition according to any one of embodiments 22, or 24-27 wherein the enzyme is a lipoxygenase.

30. The composition according to any one of embodiments 22, or 24-27 wherein the enzyme is a monooxygenase.

31. The composition according to any one of embodiments 22, or 24-30 wherein the enzyme does not require adenosine triphosphate (ATP) for catalytic activity.

32. The composition according to any one of embodiments 22, or 24-31 comprising a plurality of enzymes.

33. The composition according to embodiment 32 wherein the plurality of enzymes comprises a dioxygenase, monooxygenase, heme peroxidase, and/or P450.

34. The composition according to any one of embodiments 22, or 25-33 wherein the enzyme is a cyanobacterial enzyme.

35. The composition according to any one of embodiments 22, or 25-33 wherein the enzyme catalyzes beta or omega oxidation.

36. The composition according to any one of embodiments 22, or 25-33 wherein the enzyme has activity at the 10S and/or 12S-carbon of an oleic acid.

37. The composition according to embodiment 23 wherein the polypeptide forms a complex with the fatty acid.

38. The composition according to embodiment 23 wherein the polypeptide inhibits reactivity of the fatty acid.

39. The composition according to embodiment 23 wherein the polypeptide inhibits diffusion of the fatty acid.

40. A composition comprising one or more enzymes according to any one of embodiments 22, or 25-33 and one or more polypeptides according to any one of embodiments 23, or 37-39.

41. The method or composition according to any one of embodiments 1-2, or 22 wherein the enzyme comprises an amino acid sequence of SEQ ID NO: 1 or a circular permutated variant thereof.

42. The method or composition according to any one of embodiments 1-2, or 22 wherein the enzyme comprises an amino acid sequence of SEQ ID NO: 2 or a circular permutated variant thereof.

43. The method or composition according to any one of embodiments 1-2, or 22 wherein the enzyme comprises an amino acid sequence of SEQ ID NO: 3 or a circular permutated variant thereof.

44. The method or composition according to any one of embodiments 1-2, or 22 wherein the enzyme comprises an amino acid sequence of SEQ ID NO: 4 or a circular permutated variant thereof.

45. The method or composition according to any one of embodiments 1-2, or 22 wherein the enzyme comprises an amino acid sequence of SEQ ID NO: 5 or a circular permutated variant thereof.

46. The method or composition according to any one of embodiments 1-2, or 22 wherein the enzyme comprises an amino acid sequence of SEQ ID NO: 6 or a circular permutated variant thereof.

47. The method or composition according to any one of embodiments 1-2, or 22 wherein the enzyme comprises an amino acid sequence of SEQ ID NO: 7 or a circular permutated variant thereof.

48. The method or composition according to any one of embodiments 1-2, or 22 wherein the enzyme comprises an amino acid sequence of SEQ ID NO: 8 or a circular permutated variant thereof.

48. The method or composition according to any one of embodiments 1-2, or 22 wherein the enzyme comprises an amino acid sequence of SEQ ID NO: 9 or a circular permutated variant thereof.

49. The method or composition according to any one of embodiments 1-2, or 22 wherein the enzyme comprises an amino acid sequence of SEQ ID NO: 10 or a circular permutated variant thereof.

50. The method or composition according to any one of embodiments 1-2, or 22 wherein the enzyme comprises an amino acid sequence of SEQ ID NO: 11 or a circular permutated variant thereof.

51. The method or composition according to any one of embodiments 1-2, or 22 wherein the enzyme comprises an amino acid sequence of SEQ ID NO: 12 or a circular permutated variant thereof.

52. The method or composition according to any one of embodiments 1-2, or 22 wherein the enzyme comprises an amino acid sequence of any one of SEQ ID NOs: 13-15, or a circular permutated variant thereof.

Having thus described at least several aspects and embodiments of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in further detail by the claims that follow.

EQUIVALENTS

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

What is claimed is:

1. A host cell that comprises a heterologous polynucleotide encoding a lipoxygenase, wherein the lipoxygenase comprises an amino acid sequence that is at least 90% identical to SEQ ID NO: 1, and wherein the lipoxygenase has activity at the 10S-carbon of one or more fatty acids.

2. The host cell of claim 1, wherein the lipoxygenase comprises SEQ ID NO: 1.

3. The host cell of claim 1, wherein the lipoxygenase promotes breakdown of the one or more fatty acids.

4. The host cell of claim 3, wherein one or more of the fatty acids is an oleic acid and/or a linoleic acid.

5. The host cell of claim 1, wherein the host cell is a plant cell, a fungal cell, a yeast cell, a bacterial cell, or an animal cell.

6. The host cell of claim 5, wherein the bacterial cell is an *Escherichia coli* cell.

7. A method comprising culturing the host cell of claim 1.

8. The host cell of claim 3, wherein one or more of the fatty acids is unsaturated.

9. The host cell of claim 1, wherein the lipoxygenase has activity at the 12S-carbon of an oleic acid.

10. The host cell of claim 1, wherein the lipoxygenase is capable of promoting the breakdown of one or more fatty acids in bodily fluid secreted from a human.

11. The host cell of claim 10, wherein the bodily fluid comprises sweat or sebum.

* * * * *

SEQUENCE LISTING

```
<160> NUMBER OF SEQ ID NOS: 15

<210> SEQ ID NO 1
<211> LENGTH: 547
<212> TYPE: PRT
<213> ORGANISM: Oscillatoria nigro-viridis

<400> SEQUENCE: 1

Thr Arg Asp Thr Ser Arg Asp Gly Phe Ser Asn Lys Ala Leu Ala Tyr
1               5                   10                  15

Thr Leu Thr His Phe Lys Pro Ile Trp Asn Leu Val Gln Ser Tyr Glu
            20                  25                  30

Pro Leu Lys Arg Lys Leu Asn Lys Phe Phe Leu Asn Ser Ile Ile Tyr
        35                  40                  45

Lys Leu Pro Thr Arg Pro Leu Pro Tyr Ser Leu Met Gly Leu Asp Pro
```

```
            50                  55                  60
Lys Ile Pro Gly Thr Asp Ile Pro Lys Lys Thr Asp Thr Tyr Ile Ser
 65                  70                  75                  80

Trp Asp Ser Leu Thr Asp Lys Thr Tyr Thr Gly Arg His Leu Pro Pro
                 85                  90                  95

Asp Pro Glu Phe Asn Lys Glu Gly Asn Leu Pro Pro Leu Asp Lys Val
            100                 105                 110

Lys Thr Leu Phe Gln Lys Arg Asp Gly Lys Thr Ile Tyr Ser Glu Lys
            115                 120                 125

Ser Thr Leu Leu Phe Pro Tyr Trp Val Gln Trp Phe Thr Asp Ser Phe
            130                 135                 140

Leu Arg Ile Asp Gln Glu Asn Arg Phe Lys Asn Thr Ser Asn His Gln
145                 150                 155                 160

Ile Asp Met Cys Asn Val Tyr Gly Leu Thr Arg Lys Gln Thr Asn Met
                165                 170                 175

Leu Arg Ala Phe Lys Asp Gly Lys Phe Lys Thr Gln Lys Leu Lys Arg
                180                 185                 190

Lys Asp Gly Val Glu Glu Tyr Pro Leu Phe Tyr Tyr Ala Asp Pro
                195                 200                 205

Glu Gln Gly Ile Ile Asp Pro Gln Phe Glu Gly Leu His Ala Pro Leu
    210                 215                 220

Asn Asp Glu Lys Arg Gln Pro Pro Glu Lys Lys Ser Lys Leu Phe Ala
225                 230                 235                 240

Met Gly Val Glu Arg Ala Asn Val Gln Ile Gly Tyr Val Met Leu Asn
                245                 250                 255

Thr Leu Cys Ile Arg Glu His Asn Arg Ile Cys Asp Val Leu Ser Lys
                260                 265                 270

Ser Tyr Pro Glu Trp Asp Glu Arg Leu Phe Gln Thr Ala Arg Asn
                275                 280                 285

Ile Leu Met Val Ile Val Leu Asn Ile Ile Met Glu Glu Tyr Ile Phe
    290                 295                 300

His Ile Thr Pro Tyr Asn Phe Arg Phe Phe Ala Asp Pro Glu Ala Phe
305                 310                 315                 320

Thr Lys Glu Ser Trp Tyr Arg Glu Asn Trp Met Ala Ile Glu Phe Ser
                325                 330                 335

Phe Val Tyr Arg Trp His Ser Ala Ile Pro Glu Thr Phe Ile Tyr Asp
                340                 345                 350

Gly Lys Glu Gln Ser Met Tyr Asp Ser Leu Trp Asn Asn Gln Met Leu
                355                 360                 365

Ile Asp Lys Gly Leu Gly Ala Leu Met Glu Glu Thr Cys Ser Gln Pro
    370                 375                 380

Gly Thr Arg Ile Gly Leu Phe Asn Thr Pro Asp Phe Lys Ile Ala Gly
385                 390                 395                 400

Thr Pro Tyr Thr Phe Ile Asp Ala Thr Glu Leu Ala Ser Val Lys Leu
                405                 410                 415

Gly Arg Gln Ala Gln Leu Ala Ser Tyr Asn Asp Tyr Arg Glu Met Cys
                420                 425                 430

Gly Tyr Pro Arg Val Thr Asp Phe Asn Gln Ile Thr Gly Asp Glu Tyr
                435                 440                 445

Ala Gln Gln Lys Leu Lys Glu Leu Tyr Gly His Val Asp Lys Ile Glu
    450                 455                 460

Leu Phe Val Gly Leu Tyr Ala Glu Asp Val Arg Lys Asn Ser Ala Ile
465                 470                 475                 480
```

```
Pro Pro Leu Val Ala Arg Ile Gly Ile Asp Ala Phe Ser Gln Ala
            485                 490                 495

Leu Thr Asn Pro Leu Leu Ser Pro Lys Val Phe Asn Lys Glu Thr Phe
            500                 505                 510

Ser Glu Val Gly Trp Glu Ile Ile Gln Asn Thr Lys Thr Val Ser Asp
            515                 520                 525

Leu Val Asn Arg Asn Val Pro Pro Ser Asp Pro Lys Tyr Lys Val Ser
            530                 535                 540

Phe Glu Leu
545

<210> SEQ ID NO 2
<211> LENGTH: 540
<212> TYPE: PRT
<213> ORGANISM: Synechocystis PCC7509

<400> SEQUENCE: 2

Arg Asp Thr Ser Lys Asp Gly Phe Arg Asn Lys Leu Glu Thr Tyr Ala
1               5                   10                  15

Leu Thr His Phe Lys Pro Ile Trp Asn Leu Ile Gln Ser Asn Asp Thr
            20                  25                  30

Leu Lys Lys Lys Val Asn Lys Phe Leu Val Asn Asn Ala Ile Tyr Lys
        35                  40                  45

Val Pro Thr Arg Pro Tyr Pro Phe Ser Thr Met Ser Pro Tyr Thr Ser
    50                  55                  60

Trp Asp Ser Leu Ser Asp Arg Thr Tyr Ser Gly Leu His Leu Pro Pro
65                  70                  75                  80

Leu Asp Trp Gln Pro Leu Thr Asn Glu Asn His Leu Lys Leu Lys Leu
                85                  90                  95

Ala Asp Thr Lys Asp Phe Glu Lys Lys Leu Pro Ala Ile Glu Asp Leu
            100                 105                 110

Arg Gly Leu Tyr Arg Lys Ser Gly Glu Thr Lys Tyr Ser Pro Lys Ser
        115                 120                 125

Thr Leu Ile Phe Pro Tyr Phe Val Gln Trp Phe Thr Asp Ser Phe Leu
    130                 135                 140

Arg Thr Asp Arg His Asn His Arg Lys Asn Thr Ser Asn His Gln Ile
145                 150                 155                 160

Asp Leu Cys Thr Val Tyr Gly Leu Asn Ala Lys Ile Thr His Leu Leu
                165                 170                 175

Arg Ser Tyr Gln Gly Gly Lys Leu Lys Ser Gln Ile Ile Asn Gly Glu
            180                 185                 190

Glu Tyr Pro Pro Phe Tyr Tyr Asp Glu Lys Gly Glu Ala Lys Lys Glu
        195                 200                 205

Phe Ile Gly Leu Pro His Gln Leu Asp Asn Asp Gly Asn Pro Lys Ala
    210                 215                 220

Asp Thr Phe Pro Leu Asp Lys Lys Gln Lys Leu Phe Ala Met Gly Val
225                 230                 235                 240

Glu Val Glu Arg Ser Asn Val Gln Ile Gly Tyr Val Met Leu Asn Val
                245                 250                 255

Leu Ala Leu Arg Glu His Asn Arg Leu Cys Glu Leu Leu Ala Lys Thr
            260                 265                 270

Tyr Pro Ser Trp Asp Asp Glu Arg Leu Phe Gln Thr Ala Arg Asn Ile
        275                 280                 285

Leu Ile Val Glu Val Leu Arg Ile Val Val Glu Asp Tyr Val Asn His
```

```
            290                 295                 300
Ile Thr Pro Tyr His Phe Gln Phe Ile Thr Asp Pro Leu Thr Phe Ser
305                 310                 315                 320

Asn Glu Lys Trp Tyr Arg Gln Asn Trp Met Thr Val Glu Phe Thr Leu
                325                 330                 335

Val Tyr Arg Trp His Ser Met Leu Pro Asp Thr Leu Ile Tyr Asn Gly
            340                 345                 350

Gln Lys Ile Pro Thr Tyr Glu Thr Gln Trp Asn Asn Glu Met Ile Ile
        355                 360                 365

Lys Gln Gly Leu Gly Ala Leu Phe Glu Glu Ser Cys Ser Gln Pro Cys
370                 375                 380

Ala Gln Leu Ser Leu Phe Asn Thr Pro Glu Phe Leu Ile Pro Val Glu
385                 390                 395                 400

Leu Ala Ser Val Arg Phe Gly Arg Glu Val Lys Leu Arg Ser Tyr Asn
                405                 410                 415

Asp Tyr Arg Gln Leu Cys Lys Tyr Pro Arg Val Thr Asp Phe Asp Gln
            420                 425                 430

Ile Ser Ser Asp Lys Asn Ile Gln Lys Glu Leu Gln Arg Leu Tyr Gly
        435                 440                 445

His Val Asp Asn Ile Glu Leu Tyr Val Gly Ile Tyr Ala Glu Asp Leu
    450                 455                 460

Arg Glu Asn Ser Ala Leu Pro Ser Leu Val Gly Arg Leu Ile Gly Ile
465                 470                 475                 480

Asp Ala Phe Ser Gln Val Leu Thr Asn Pro Leu Leu Ala Glu Ser Val
                485                 490                 495

Phe His Pro Glu Thr Phe Ser Pro Val Gly Trp Glu Ile Gln Asn
            500                 505                 510

Thr Lys Thr Leu Ser Gln Leu Leu His Arg Asn Leu Pro Pro Ser Asp
        515                 520                 525

Lys Lys Tyr Arg Val Ser Phe Asp Arg Ala Ser Thr
    530                 535                 540

<210> SEQ ID NO 3
<211> LENGTH: 543
<212> TYPE: PRT
<213> ORGANISM: Tolypothrix campylonemoides

<400> SEQUENCE: 3

Ala Gly Lys Arg Asp Thr Ser Lys Asp Gly Phe Asp Asn Lys Val Gln
1               5                   10                  15

Thr Phe Leu Leu Thr Asn Phe Lys Gly Ile Trp Glu Ile Val Gln Ser
                20                  25                  30

Asn Glu Phe Leu Lys Arg Lys Val Asn Lys Thr Leu Ile Asn Ser Leu
            35                  40                  45

Ile Tyr Lys Ile Pro Thr Arg Pro Asn Pro Tyr Ser Met Met Thr Leu
        50                  55                  60

Asp Glu Tyr Ile Pro Asp Thr Lys Ile Pro Lys Lys Thr Asp Thr Tyr
65                  70                  75                  80

Thr Ser Trp Glu Leu Leu Asn Asp Arg Thr Tyr Ile Gly Arg His Leu
                85                  90                  95

Pro Pro Asp Pro Lys Phe Asn Ser Glu Gly Asn Leu Pro Lys Val Glu
            100                 105                 110

Asp Leu Ala Val Leu Phe Arg Lys Arg Asp Gly Lys Thr Ile Tyr Ser
        115                 120                 125
```

```
Pro Lys Ser Thr Met Leu Phe Pro Tyr Trp Val Gln Trp Phe Thr Asp
130                 135                 140

Ser Phe Leu Arg Ile Asp His Thr Lys Glu Lys Lys Leu Lys Asn Thr
145                 150                 155                 160

Ser Asn His Glu Ile Asp Leu Cys Asn Val Tyr Gly Leu Asn Arg Lys
                165                 170                 175

Arg Thr His Leu Leu Arg Thr Phe Lys Gly Lys Phe Lys Thr Gln
            180                 185                 190

Lys Leu Lys Arg Gln Asp Gly Ile Glu Glu Tyr Pro Leu Phe Tyr
        195                 200                 205

Tyr Ala Asp Pro Ala Gln Gly Ile Val Asp Pro Gln Phe Asp Gly Leu
210                 215                 220

Tyr Glu Pro Ile Asn Asp Glu Lys Arg Leu Pro Ala Asp Lys Lys Gln
225                 230                 235                 240

Tyr Leu Phe Ala Met Gly Val Glu Arg Ala Asn Val Gln Ile Gly Tyr
                245                 250                 255

Val Met Leu Asn Thr Leu Cys Ile Arg Glu His Asn Arg Leu Cys Asp
            260                 265                 270

Glu Leu Ala Ser Asn Tyr Pro Asp Trp Asp Asp Glu Arg Leu Phe Gln
        275                 280                 285

Thr Ser Arg Asn Ile Leu Met Ala Ile Ile Leu Asn Ile Ile Met Glu
290                 295                 300

Glu Tyr Ile Asn His Ile Thr Pro Tyr His Phe Lys Leu Phe Ala Asp
305                 310                 315                 320

Pro Ala Ala Phe Val Lys Glu Ser Trp Tyr Arg Pro Asn Trp Met Thr
                325                 330                 335

Ile Glu Phe Asp Phe Val Tyr Arg Trp His Ser Ala Ile Pro Glu Thr
            340                 345                 350

Phe Ile Tyr Asp Gly Gln Pro Thr Asp Ile Ala Ala Ser Leu Trp Asn
        355                 360                 365

Asn Lys Met Phe Ile Asp Lys Gly Leu Gly Ala Leu Met Glu Glu Thr
370                 375                 380

Cys Ser Gln Pro Gly Thr Arg Ile Gly Leu Phe Asn Thr Pro Asp Ile
385                 390                 395                 400

Leu Val Glu Leu Thr Glu Leu Pro Ser Ile Arg Leu Gly Arg Gln Leu
                405                 410                 415

Gln Leu Ala Ser Tyr Asn Asp Tyr Arg Glu Met Cys Gly Phe Pro Arg
            420                 425                 430

Val Thr Lys Phe Glu Gln Ile Thr Gly Asp Glu Phe Ala Gln Glu Lys
        435                 440                 445

Leu Lys Glu Leu Tyr Gly His Val Asp Asn Ile Glu Phe Tyr Val Gly
450                 455                 460

Leu Tyr Ala Glu Glu Val Arg Lys Asn Ser Thr Ile Pro Pro Leu Val
465                 470                 475                 480

Ala Arg Leu Ile Gly Ile Asp Ala Phe Ser Glu Ala Leu Asn Asn Pro
                485                 490                 495

Leu Leu Ser Pro Thr Ile Phe Asn Lys Asp Thr Phe Ser Pro Val Gly
            500                 505                 510

Trp Glu Ile Ile Gln Asn Thr Lys Thr Val Ser Asp Leu Ile Asn Arg
        515                 520                 525

Asn Val Pro Pro Ser Asp Lys Lys Tyr Lys Val Thr Phe Asp Leu
530                 535                 540
```

```
<210> SEQ ID NO 4
<211> LENGTH: 547
<212> TYPE: PRT
<213> ORGANISM: Artificial Sequence
<220> FEATURE:
<223> OTHER INFORMATION: Engineered prostaglandin endoperoxide synthase

<400> SEQUENCE: 4
```

Thr Arg Asp Thr Ser Arg Asp Gly Phe Ser Asn Lys Ala Leu Ala Tyr
1               5                   10                  15

Thr Leu Thr His Phe Lys Pro Ile Trp Asn Leu Val Gln Ser Tyr Glu
            20                  25                  30

Pro Leu Lys Arg Lys Leu Asn Lys Phe Phe Leu Asn Ser Ile Ile Tyr
        35                  40                  45

Lys Leu Pro Thr Arg Pro Leu Pro Tyr Ser Leu Met Gly Leu Asp Pro
    50                  55                  60

Lys Ile Pro Gly Thr Asp Ile Pro Lys Lys Thr Asp Thr Tyr Ile Ser
65                  70                  75                  80

Trp Asp Ser Leu Thr Asp Lys Thr Tyr Thr Gly Arg His Leu Pro Pro
                85                  90                  95

Asp Pro Glu Phe Asn Lys Glu Gly Asn Leu Pro Pro Leu Asp Lys Val
            100                 105                 110

Lys Thr Leu Phe Gln Lys Arg Asp Gly Lys Thr Ile Tyr Ser Glu Lys
        115                 120                 125

Ser Thr Leu Leu Phe Pro Tyr Trp Val Gln Trp Phe Thr Asp Ser Phe
    130                 135                 140

Leu Arg Ile Asp Gln Glu Asn Arg Phe Lys Asn Thr Ser Asn His Gln
145                 150                 155                 160

Ile Asp Met Cys Asn Val Tyr Gly Leu Thr Arg Lys Gln Thr Asn Met
                165                 170                 175

Leu Arg Ala Phe Lys Asp Gly Lys Phe Lys Thr Gln Lys Leu Lys Arg
            180                 185                 190

Lys Asp Gly Val Glu Glu Tyr Pro Leu Phe Tyr Tyr Ala Asp Pro
        195                 200                 205

Glu Gln Gly Ile Ile Asp Pro Gln Phe Glu Gly Leu His Ala Pro Leu
    210                 215                 220

Asn Asp Glu Lys Arg Gln Pro Pro Glu Lys Lys Ser Lys Leu Phe Ala
225                 230                 235                 240

Met Gly Val Glu Arg Ala Asn Val Gln Ile Gly Tyr Val Met Leu Asn
                245                 250                 255

Thr Leu Cys Ile Arg Glu His Asn Arg Ile Cys Asp Val Leu Ser Lys
            260                 265                 270

Ser Tyr Pro Glu Trp Asp Asp Glu Arg Leu Phe Gln Thr Ala Arg Asn
        275                 280                 285

Ile Leu Met Val Ile Val Leu Asn Ile Ile Met Glu Glu Tyr Ile Phe
    290                 295                 300

His Ile Thr Pro Tyr Asn Phe Arg Phe Ala Asp Pro Glu Ala Phe
305                 310                 315                 320

Thr Lys Glu Ser Trp Tyr Arg Glu Asn Trp Met Ala Ile Glu Phe Ser
                325                 330                 335

Phe Val Tyr Arg Trp His Ser Ala Ile Pro Glu Thr Phe Ile Tyr Asp
            340                 345                 350

Gly Lys Glu Gln Ser Met Tyr Asp Ser Leu Trp Asn Asn Gln Met Leu
        355                 360                 365

Ile Asp Lys Gly Leu Gly Ala Leu Met Glu Glu Thr Cys Ser Gln Pro

```
             370                 375                 380
Gly Thr Arg Ile Gly Leu Phe Asn Thr Pro Asp Phe Lys Ile Ala Gly
385                 390                 395                 400

Thr Pro Tyr Thr Phe Ile Asp Ala Thr Glu Leu Ala Ser Val Lys Leu
                405                 410                 415

Gly Arg Gln Ala Gln Leu Ala Ser Tyr Asn Asp Tyr Arg Glu Met Cys
            420                 425                 430

Gly Tyr Pro Arg Val Thr Asp Phe Asn Gln Ile Thr Gly Asp Glu Tyr
        435                 440                 445

Ala Gln Gln Lys Leu Lys Glu Leu Tyr Gly His Val Asp Lys Ile Glu
    450                 455                 460

Leu Phe Val Gly Leu Tyr Ala Glu Asp Val Arg Lys Asn Ser Ala Ile
465                 470                 475                 480

Pro Pro Leu Val Ala Arg Ile Ile Gly Ile Asp Ala Phe Ser Gln Ala
                485                 490                 495

Leu Thr Asn Pro Leu Leu Ser Pro Lys Val Phe Asn Lys Glu Thr Phe
            500                 505                 510

Ser Glu Val Gly Trp Glu Ile Ile Gln Asn Thr Lys Thr Val Ser Asp
        515                 520                 525

Leu Val Asn Arg Asn Val Pro Pro Ser Asp Pro Lys Tyr Lys Val Ser
    530                 535                 540

Phe Glu Glu
545

<210> SEQ ID NO 5
<211> LENGTH: 540
<212> TYPE: PRT
<213> ORGANISM: Artificial Sequence
<220> FEATURE:
<223> OTHER INFORMATION: Engineered heme peroxidase

<400> SEQUENCE: 5

Arg Asp Thr Ser Lys Asp Gly Phe Arg Asn Lys Leu Glu Thr Tyr Ala
1               5                   10                  15

Leu Thr His Phe Lys Pro Ile Trp Asn Leu Ile Gln Ser Asn Asp Thr
            20                  25                  30

Leu Lys Lys Lys Val Asn Lys Phe Leu Val Asn Asn Ala Ile Tyr Lys
        35                  40                  45

Val Pro Thr Arg Pro Tyr Pro Phe Ser Thr Met Ser Pro Tyr Thr Ser
    50                  55                  60

Trp Asp Ser Leu Ser Asp Arg Thr Tyr Ser Gly Leu His Leu Pro Pro
65                  70                  75                  80

Leu Asp Trp Gln Pro Leu Thr Asn Glu Asn His Leu Lys Leu Lys Leu
                85                  90                  95

Ala Asp Thr Lys Asp Phe Glu Lys Lys Leu Pro Ala Ile Glu Asp Leu
            100                 105                 110

Arg Gly Leu Tyr Arg Lys Ser Gly Glu Thr Lys Tyr Ser Pro Lys Ser
        115                 120                 125

Thr Leu Ile Phe Pro Tyr Phe Val Gln Trp Phe Thr Asp Ser Phe Leu
    130                 135                 140

Arg Thr Asp Arg His Asn His Arg Lys Asn Thr Ser Asn His Gln Ile
145                 150                 155                 160

Asp Leu Cys Thr Val Tyr Gly Leu Asn Ala Lys Ile Thr His Leu Leu
                165                 170                 175

Arg Ser Tyr Gln Gly Gly Lys Leu Lys Ser Gln Ile Ile Asn Gly Glu
```

```
                180                 185                 190
Glu Tyr Pro Pro Phe Tyr Tyr Asp Glu Lys Gly Glu Ala Lys Lys Glu
            195                 200                 205

Phe Ile Gly Leu Pro His Gln Leu Asp Asn Asp Gly Asn Pro Lys Ala
        210                 215                 220

Asp Thr Phe Pro Leu Asp Lys Lys Gln Lys Leu Phe Ala Met Gly Val
225                 230                 235                 240

Glu Val Glu Arg Ser Asn Val Gln Ile Gly Tyr Val Met Leu Asn Val
            245                 250                 255

Leu Ala Leu Arg Glu His Asn Arg Leu Cys Glu Leu Leu Ala Lys Thr
        260                 265                 270

Tyr Pro Ser Trp Asp Asp Glu Arg Leu Phe Gln Thr Ala Arg Asn Ile
    275                 280                 285

Leu Ile Val Glu Val Leu Arg Ile Val Val Glu Asp Tyr Val Asn His
290                 295                 300

Ile Thr Pro Tyr His Phe Gln Phe Ile Thr Asp Pro Leu Thr Phe Ser
305                 310                 315                 320

Asn Glu Lys Trp Tyr Arg Gln Asn Trp Met Thr Val Glu Phe Thr Leu
            325                 330                 335

Val Tyr Arg Trp His Ser Met Leu Pro Asp Thr Leu Ile Tyr Asn Gly
        340                 345                 350

Gln Lys Ile Pro Thr Tyr Glu Thr Gln Trp Asn Asn Glu Met Ile Ile
    355                 360                 365

Lys Gln Gly Leu Gly Ala Leu Phe Glu Glu Ser Cys Ser Gln Pro Cys
370                 375                 380

Ala Gln Leu Ser Leu Phe Asn Thr Pro Glu Phe Leu Ile Pro Val Glu
385                 390                 395                 400

Leu Ala Ser Val Arg Phe Gly Arg Glu Val Lys Leu Arg Ser Tyr Asn
            405                 410                 415

Asp Tyr Arg Gln Leu Cys Lys Tyr Pro Arg Val Thr Asp Phe Asp Gln
        420                 425                 430

Ile Ser Ser Asp Lys Asn Ile Gln Lys Glu Leu Gln Arg Leu Tyr Gly
    435                 440                 445

His Val Asp Asn Ile Glu Leu Tyr Val Gly Ile Tyr Ala Glu Asp Leu
450                 455                 460

Arg Glu Asn Ser Ala Leu Pro Ser Leu Val Gly Arg Leu Ile Gly Ile
465                 470                 475                 480

Asp Ala Phe Ser Gln Val Leu Thr Asn Pro Leu Leu Ala Glu Ser Val
            485                 490                 495

Phe His Pro Glu Thr Phe Ser Pro Val Gly Trp Glu Ile Gln Asn
        500                 505                 510

Thr Lys Thr Leu Ser Gln Leu Leu His Arg Asn Leu Pro Pro Ser Asp
    515                 520                 525

Lys Lys Tyr Arg Val Ser Phe Asp Arg Ala Ser Glu
530                 535                 540

<210> SEQ ID NO 6
<211> LENGTH: 543
<212> TYPE: PRT
<213> ORGANISM: Artificial Sequence
<220> FEATURE:
<223> OTHER INFORMATION: Engineered heme peroxidase

<400> SEQUENCE: 6

Ala Gly Lys Arg Asp Thr Ser Lys Asp Gly Phe Asp Asn Lys Val Gln
```

-continued

```
1               5                   10                  15
Thr Phe Leu Leu Thr Asn Phe Lys Gly Ile Trp Glu Ile Val Gln Ser
                20                  25                  30

Asn Glu Phe Leu Lys Arg Lys Val Asn Lys Thr Leu Ile Asn Ser Leu
                35                  40                  45

Ile Tyr Lys Ile Pro Thr Arg Pro Asn Pro Tyr Ser Met Met Thr Leu
                50                  55                  60

Asp Glu Tyr Ile Pro Asp Thr Lys Ile Pro Lys Lys Thr Asp Thr Tyr
65                  70                  75                  80

Thr Ser Trp Glu Leu Leu Asn Asp Arg Thr Tyr Ile Gly Arg His Leu
                    85                  90                  95

Pro Pro Asp Pro Lys Phe Asn Ser Glu Gly Asn Leu Pro Lys Val Glu
                100                 105                 110

Asp Leu Ala Val Leu Phe Arg Lys Arg Asp Gly Lys Thr Ile Tyr Ser
                115                 120                 125

Pro Lys Ser Thr Met Leu Phe Pro Tyr Val Gln Trp Phe Thr Asp
                130                 135                 140

Ser Phe Leu Arg Ile Asp His Thr Lys Glu Lys Leu Lys Asn Thr
145                 150                 155                 160

Ser Asn His Glu Ile Asp Leu Cys Asn Val Tyr Gly Leu Asn Arg Lys
                    165                 170                 175

Arg Thr His Leu Leu Arg Thr Phe Lys Gly Gly Lys Phe Lys Thr Gln
                180                 185                 190

Lys Leu Lys Arg Gln Asp Gly Ile Glu Glu Glu Tyr Pro Leu Phe Tyr
                195                 200                 205

Tyr Ala Asp Pro Ala Gln Gly Ile Val Asp Pro Gln Phe Asp Gly Leu
210                 215                 220

Tyr Glu Pro Ile Asn Asp Glu Lys Arg Leu Pro Ala Asp Lys Lys Gln
225                 230                 235                 240

Tyr Leu Phe Ala Met Gly Val Glu Arg Ala Asn Val Gln Ile Gly Tyr
                245                 250                 255

Val Met Leu Asn Thr Leu Cys Ile Arg Glu His Asn Arg Leu Cys Asp
                260                 265                 270

Glu Leu Ala Ser Asn Tyr Pro Asp Trp Asp Asp Glu Arg Leu Phe Gln
                275                 280                 285

Thr Ser Arg Asn Ile Leu Met Ala Ile Ile Leu Asn Ile Ile Met Glu
                290                 295                 300

Glu Tyr Ile Asn His Ile Thr Pro Tyr His Phe Lys Leu Phe Ala Asp
305                 310                 315                 320

Pro Ala Ala Phe Val Lys Glu Ser Trp Tyr Arg Pro Asn Trp Met Thr
                325                 330                 335

Ile Glu Phe Asp Phe Val Tyr Arg Trp His Ser Ala Ile Pro Glu Thr
                340                 345                 350

Phe Ile Tyr Asp Gly Gln Pro Thr Asp Ile Ala Ala Ser Leu Trp Asn
                355                 360                 365

Asn Lys Met Phe Ile Asp Lys Gly Leu Gly Ala Leu Met Glu Glu Thr
                370                 375                 380

Cys Ser Gln Pro Gly Thr Arg Ile Gly Leu Phe Asn Thr Pro Asp Ile
385                 390                 395                 400

Leu Val Glu Leu Thr Glu Leu Pro Ser Ile Arg Leu Gly Arg Gln Leu
                405                 410                 415

Gln Leu Ala Ser Tyr Asn Asp Tyr Arg Glu Met Cys Gly Phe Pro Arg
                420                 425                 430
```

```
Val Thr Lys Phe Glu Gln Ile Thr Gly Asp Glu Phe Ala Gln Glu Lys
        435                 440                 445

Leu Lys Glu Leu Tyr Gly His Val Asp Asn Ile Glu Phe Tyr Val Gly
    450                 455                 460

Leu Tyr Ala Glu Glu Val Arg Lys Asn Ser Thr Ile Pro Pro Leu Val
465                 470                 475                 480

Ala Arg Leu Ile Gly Ile Asp Ala Phe Ser Glu Ala Leu Asn Pro
                485                 490                 495

Leu Leu Ser Pro Thr Ile Phe Asn Lys Asp Thr Phe Ser Pro Val Gly
                500                 505                 510

Trp Glu Ile Ile Gln Asn Thr Lys Thr Val Ser Asp Leu Ile Asn Arg
                515                 520                 525

Asn Val Pro Pro Ser Asp Lys Lys Tyr Lys Val Thr Phe Asp Glu
        530                 535                 540
```

<210> SEQ ID NO 7
<211> LENGTH: 547
<212> TYPE: PRT
<213> ORGANISM: Artificial Sequence
<220> FEATURE:
<223> OTHER INFORMATION: Engineered prostaglandin-endoperoxide synthase

<400> SEQUENCE: 7

```
Thr Arg Asp Thr Ser Arg Asp Gly Phe Ser Asn Lys Ala Leu Ala Tyr
1               5                   10                  15

Thr Leu Thr His Phe Lys Pro Ile Trp Asn Leu Val Gln Ser Tyr Glu
            20                  25                  30

Pro Leu Lys Arg Lys Leu Asn Lys Phe Phe Leu Asn Ser Ile Ile Tyr
        35                  40                  45

Lys Leu Pro Thr Arg Pro Leu Pro Tyr Ser Leu Met Gly Leu Asp Pro
    50                  55                  60

Lys Ile Pro Gly Thr Asp Ile Pro Lys Lys Thr Asp Thr Tyr Ile Ser
65                  70                  75                  80

Trp Asp Ser Leu Thr Asp Lys Thr Tyr Thr Gly Arg His Leu Pro Pro
                85                  90                  95

Asp Pro Glu Phe Asn Lys Glu Gly Asn Leu Pro Pro Leu Asp Lys Val
            100                 105                 110

Lys Thr Leu Phe Gln Lys Arg Asp Gly Lys Thr Ile Tyr Ser Glu Lys
        115                 120                 125

Ser Thr Leu Leu Phe Pro Tyr Trp Val Gln Trp Phe Thr Asp Ser Phe
    130                 135                 140

Leu Arg Ile Asp Gln Glu Asn Arg Phe Lys Asn Thr Ser Asn His Gln
145                 150                 155                 160

Ile Asp Met Cys Asn Val Tyr Gly Leu Thr Arg Lys Gln Thr Asn Met
                165                 170                 175

Leu Arg Ala Phe Lys Asp Gly Lys Phe Lys Thr Gln Lys Leu Lys Arg
            180                 185                 190

Lys Asp Gly Val Glu Glu Tyr Pro Leu Phe Tyr Tyr Ala Asp Pro
        195                 200                 205

Glu Gln Gly Ile Ile Asp Pro Gln Phe Glu Gly Leu His Ala Pro Leu
    210                 215                 220

Asn Asp Glu Lys Arg Gln Pro Pro Glu Lys Lys Ser Lys Leu Phe Ala
225                 230                 235                 240

Met Gly Val Glu Arg Ala Asn Val Gln Ile Gly Tyr Val Met Leu Asn
                245                 250                 255
```

-continued

```
Thr Leu Cys Ile Arg Glu His Asn Arg Ile Cys Asp Val Leu Ser Lys
        260                 265                 270

Ser Tyr Pro Glu Trp Asp Asp Glu Arg Leu Phe Gln Thr Ala Arg Asn
    275                 280                 285

Ile Leu Met Val Ile Val Leu Asn Ile Ile Met Glu Glu Tyr Ile Phe
        290                 295                 300

His Ile Thr Pro Tyr Asn Phe Arg Phe Phe Ala Asp Pro Glu Ala Phe
305                 310                 315                 320

Thr Lys Glu Ser Trp Tyr Arg Glu Asn Trp Met Ala Ile Glu Phe Ser
                325                 330                 335

Phe Val Tyr Arg Trp His Ser Ala Ile Pro Glu Thr Phe Ile Tyr Asp
            340                 345                 350

Gly Lys Glu Gln Ser Met Tyr Asp Ser Leu Trp Asn Asn Gln Met Leu
        355                 360                 365

Ile Asp Lys Gly Leu Gly Ala Leu Met Glu Glu Thr Cys Ser Gln Pro
370                 375                 380

Gly Thr Arg Ile Gly Leu Phe Asn Thr Pro Asp Phe Lys Ile Ala Gly
385                 390                 395                 400

Thr Pro Tyr Thr Phe Ile Asp Ala Thr Glu Leu Ala Ser Val Lys Leu
                405                 410                 415

Gly Arg Gln Ala Gln Leu Ala Ser Tyr Asn Asp Tyr Arg Glu Met Cys
            420                 425                 430

Gly Tyr Pro Arg Val Thr Asp Phe Asn Gln Ile Thr Gly Asp Glu Tyr
        435                 440                 445

Ala Gln Gln Lys Leu Lys Glu Leu Tyr Gly His Val Asp Lys Ile Glu
    450                 455                 460

Leu Phe Val Gly Leu Tyr Ala Glu Asp Val Arg Lys Asn Ser Ala Ile
465                 470                 475                 480

Pro Pro Leu Val Ala Arg Ile Ile Gly Ile Asp Ala Phe Ser Gln Ala
                485                 490                 495

Leu Thr Asn Pro Leu Leu Ser Pro Lys Val Phe Asn Lys Glu Thr Phe
            500                 505                 510

Ser Glu Val Gly Trp Glu Ile Ile Gln Asn Thr Lys Thr Val Ser Asp
        515                 520                 525

Leu Val Asn Arg Asn Val Pro Pro Ser Asp Pro Lys Tyr Lys Val Ser
530                 535                 540

Phe Glu Asp
545

<210> SEQ ID NO 8
<211> LENGTH: 540
<212> TYPE: PRT
<213> ORGANISM: Artificial Sequence
<220> FEATURE:
<223> OTHER INFORMATION: Engineered heme peroxidase

<400> SEQUENCE: 8

Arg Asp Thr Ser Lys Asp Gly Phe Arg Asn Lys Leu Glu Thr Tyr Ala
1               5                   10                  15

Leu Thr His Phe Lys Pro Ile Trp Asn Leu Ile Gln Ser Asn Asp Thr
            20                  25                  30

Leu Lys Lys Lys Val Asn Lys Phe Leu Val Asn Asn Ala Ile Tyr Lys
        35                  40                  45

Val Pro Thr Arg Pro Tyr Pro Phe Ser Thr Met Ser Pro Tyr Thr Ser
    50                  55                  60
```

```
Trp Asp Ser Leu Ser Asp Arg Thr Tyr Ser Gly Leu His Leu Pro Pro
 65                  70                  75                  80

Leu Asp Trp Gln Pro Leu Thr Asn Glu Asn His Leu Lys Leu Lys Leu
                 85                  90                  95

Ala Asp Thr Lys Asp Phe Glu Lys Lys Leu Pro Ala Ile Glu Asp Leu
            100                 105                 110

Arg Gly Leu Tyr Arg Lys Ser Gly Glu Thr Lys Tyr Ser Pro Lys Ser
            115                 120                 125

Thr Leu Ile Phe Pro Tyr Phe Val Gln Trp Phe Thr Asp Ser Phe Leu
            130                 135                 140

Arg Thr Asp Arg His Asn His Arg Lys Asn Thr Ser Asn His Gln Ile
145                 150                 155                 160

Asp Leu Cys Thr Val Tyr Gly Leu Asn Ala Lys Ile Thr His Leu Leu
                165                 170                 175

Arg Ser Tyr Gln Gly Gly Lys Leu Lys Ser Gln Ile Ile Asn Gly Glu
            180                 185                 190

Glu Tyr Pro Pro Phe Tyr Tyr Asp Glu Lys Gly Ala Lys Lys Glu
            195                 200                 205

Phe Ile Gly Leu Pro His Gln Leu Asp Asn Asp Gly Asn Pro Lys Ala
210                 215                 220

Asp Thr Phe Pro Leu Asp Lys Lys Gln Lys Leu Phe Ala Met Gly Val
225                 230                 235                 240

Glu Val Glu Arg Ser Asn Val Gln Ile Gly Tyr Val Met Leu Asn Val
                245                 250                 255

Leu Ala Leu Arg Glu His Asn Arg Leu Cys Glu Leu Leu Ala Lys Thr
            260                 265                 270

Tyr Pro Ser Trp Asp Asp Glu Arg Leu Phe Gln Thr Ala Arg Asn Ile
            275                 280                 285

Leu Ile Val Glu Val Leu Arg Ile Val Val Glu Asp Tyr Val Asn His
290                 295                 300

Ile Thr Pro Tyr His Phe Gln Phe Ile Thr Asp Pro Leu Thr Phe Ser
305                 310                 315                 320

Asn Glu Lys Trp Tyr Arg Gln Asn Trp Met Thr Val Glu Phe Thr Leu
                325                 330                 335

Val Tyr Arg Trp His Ser Met Leu Pro Asp Thr Leu Ile Tyr Asn Gly
            340                 345                 350

Gln Lys Ile Pro Thr Tyr Glu Thr Gln Trp Asn Asn Glu Met Ile Ile
            355                 360                 365

Lys Gln Gly Leu Gly Ala Leu Phe Glu Glu Ser Cys Ser Gln Pro Cys
            370                 375                 380

Ala Gln Leu Ser Leu Phe Asn Thr Pro Glu Phe Leu Ile Pro Val Glu
385                 390                 395                 400

Leu Ala Ser Val Arg Phe Gly Arg Glu Val Lys Leu Arg Ser Tyr Asn
                405                 410                 415

Asp Tyr Arg Gln Leu Cys Lys Tyr Pro Arg Val Thr Asp Phe Asp Gln
            420                 425                 430

Ile Ser Ser Asp Lys Asn Ile Gln Lys Glu Leu Gln Arg Leu Tyr Gly
            435                 440                 445

His Val Asp Asn Ile Glu Leu Tyr Val Gly Ile Tyr Ala Glu Asp Leu
            450                 455                 460

Arg Glu Asn Ser Ala Leu Pro Ser Leu Val Gly Arg Leu Ile Gly Ile
465                 470                 475                 480
```

```
Asp Ala Phe Ser Gln Val Leu Thr Asn Pro Leu Leu Ala Glu Ser Val
            485                 490                 495

Phe His Pro Glu Thr Phe Ser Pro Val Gly Trp Glu Glu Ile Gln Asn
        500                 505                 510

Thr Lys Thr Leu Ser Gln Leu Leu His Arg Asn Leu Pro Pro Ser Asp
        515                 520                 525

Lys Lys Tyr Arg Val Ser Phe Asp Arg Ala Ser Asp
        530                 535                 540

<210> SEQ ID NO 9
<211> LENGTH: 543
<212> TYPE: PRT
<213> ORGANISM: Artificial Sequence
<220> FEATURE:
<223> OTHER INFORMATION: Engineered heme peroxidase

<400> SEQUENCE: 9

Ala Gly Lys Arg Asp Thr Ser Lys Asp Gly Phe Asp Asn Lys Val Gln
1               5                   10                  15

Thr Phe Leu Leu Thr Asn Phe Lys Gly Ile Trp Glu Ile Val Gln Ser
            20                  25                  30

Asn Glu Phe Leu Lys Arg Lys Val Asn Lys Thr Leu Ile Asn Ser Leu
        35                  40                  45

Ile Tyr Lys Ile Pro Thr Arg Pro Asn Pro Tyr Ser Met Met Thr Leu
50                  55                  60

Asp Glu Tyr Ile Pro Asp Thr Lys Ile Pro Lys Lys Thr Asp Thr Tyr
65                  70                  75                  80

Thr Ser Trp Glu Leu Leu Asn Asp Arg Thr Tyr Ile Gly Arg His Leu
                85                  90                  95

Pro Pro Asp Pro Lys Phe Asn Ser Glu Gly Asn Leu Pro Lys Val Glu
            100                 105                 110

Asp Leu Ala Val Leu Phe Arg Lys Arg Asp Gly Lys Thr Ile Tyr Ser
        115                 120                 125

Pro Lys Ser Thr Met Leu Phe Pro Tyr Trp Val Gln Trp Phe Thr Asp
    130                 135                 140

Ser Phe Leu Arg Ile Asp His Thr Lys Glu Lys Lys Leu Lys Asn Thr
145                 150                 155                 160

Ser Asn His Glu Ile Asp Leu Cys Asn Val Tyr Gly Leu Asn Arg Lys
                165                 170                 175

Arg Thr His Leu Leu Arg Thr Phe Lys Gly Gly Lys Phe Lys Thr Gln
            180                 185                 190

Lys Leu Lys Arg Gln Asp Gly Ile Glu Glu Glu Tyr Pro Leu Phe Tyr
        195                 200                 205

Tyr Ala Asp Pro Ala Gln Gly Ile Val Asp Pro Gln Phe Asp Gly Leu
    210                 215                 220

Tyr Glu Pro Ile Asn Asp Glu Lys Arg Leu Pro Ala Asp Lys Lys Gln
225                 230                 235                 240

Tyr Leu Phe Ala Met Gly Val Glu Arg Ala Asn Val Gln Ile Gly Tyr
                245                 250                 255

Val Met Leu Asn Thr Leu Cys Ile Arg Glu His Asn Arg Leu Cys Asp
            260                 265                 270

Glu Leu Ala Ser Asn Tyr Pro Asp Trp Asp Asp Glu Arg Leu Phe Gln
        275                 280                 285

Thr Ser Arg Asn Ile Leu Met Ala Ile Ile Leu Asn Ile Ile Met Glu
    290                 295                 300
```

Glu Tyr Ile Asn His Ile Thr Pro Tyr His Phe Lys Leu Phe Ala Asp
305                 310                 315                 320

Pro Ala Ala Phe Val Lys Glu Ser Trp Tyr Arg Pro Asn Trp Met Thr
            325                 330                 335

Ile Glu Phe Asp Phe Val Tyr Arg Trp His Ser Ala Ile Pro Glu Thr
            340                 345                 350

Phe Ile Tyr Asp Gly Gln Pro Thr Asp Ile Ala Ala Ser Leu Trp Asn
            355                 360                 365

Asn Lys Met Phe Ile Asp Lys Gly Leu Gly Ala Leu Met Glu Glu Thr
            370                 375                 380

Cys Ser Gln Pro Gly Thr Arg Ile Gly Leu Phe Asn Thr Pro Asp Ile
385                 390                 395                 400

Leu Val Glu Leu Thr Glu Leu Pro Ser Ile Arg Leu Gly Arg Gln Leu
            405                 410                 415

Gln Leu Ala Ser Tyr Asn Asp Tyr Arg Glu Met Cys Gly Phe Pro Arg
            420                 425                 430

Val Thr Lys Phe Glu Gln Ile Thr Gly Asp Glu Phe Ala Gln Glu Lys
            435                 440                 445

Leu Lys Glu Leu Tyr Gly His Val Asp Asn Ile Glu Phe Tyr Val Gly
450                 455                 460

Leu Tyr Ala Glu Glu Val Arg Lys Asn Ser Thr Ile Pro Pro Leu Val
465                 470                 475                 480

Ala Arg Leu Ile Gly Ile Asp Ala Phe Ser Glu Ala Leu Asn Asn Pro
            485                 490                 495

Leu Leu Ser Pro Thr Ile Phe Asn Lys Asp Thr Phe Ser Pro Val Gly
            500                 505                 510

Trp Glu Ile Ile Gln Asn Thr Lys Thr Val Ser Asp Leu Ile Asn Arg
            515                 520                 525

Asn Val Pro Pro Ser Asp Lys Lys Tyr Lys Val Thr Phe Asp Asp
            530                 535                 540

<210> SEQ ID NO 10
<211> LENGTH: 547
<212> TYPE: PRT
<213> ORGANISM: Artificial Sequence
<220> FEATURE:
<223> OTHER INFORMATION: Engineered prostaglandin-endoperoxide synthase

<400> SEQUENCE: 10

Thr Arg Asp Thr Ser Arg Asp Gly Phe Ser Asn Lys Ala Leu Ala Tyr
1               5                   10                  15

Thr Leu Thr His Phe Lys Pro Ile Trp Asn Leu Val Gln Ser Tyr Glu
                20                  25                  30

Pro Leu Lys Arg Lys Leu Asn Lys Phe Phe Leu Asn Ser Ile Ile Tyr
            35                  40                  45

Lys Leu Pro Thr Arg Pro Leu Pro Tyr Ser Leu Met Gly Leu Asp Pro
        50                  55                  60

Lys Ile Pro Gly Thr Asp Ile Pro Lys Lys Thr Asp Thr Tyr Ile Ser
65                  70                  75                  80

Trp Asp Ser Leu Thr Asp Lys Thr Tyr Thr Gly Arg His Leu Pro Pro
                85                  90                  95

Asp Pro Glu Phe Asn Lys Glu Gly Asn Leu Pro Pro Leu Asp Lys Val
            100                 105                 110

Lys Thr Leu Phe Gln Lys Arg Asp Gly Lys Thr Ile Tyr Ser Glu Lys
        115                 120                 125

Ser Thr Leu Leu Phe Pro Tyr Trp Val Gln Trp Phe Thr Asp Ser Phe
130                 135                 140

Leu Arg Ile Asp Gln Glu Asn Arg Phe Lys Asn Thr Ser Asn His Gln
145                 150                 155                 160

Ile Asp Met Cys Asn Val Tyr Gly Leu Thr Arg Lys Gln Thr Asn Met
                165                 170                 175

Leu Arg Ala Phe Lys Asp Gly Lys Phe Lys Thr Gln Lys Leu Lys Arg
                180                 185                 190

Lys Asp Gly Val Glu Glu Tyr Pro Leu Phe Tyr Tyr Ala Asp Pro
                195                 200                 205

Glu Gln Gly Ile Ile Asp Pro Gln Phe Glu Gly Leu His Ala Pro Leu
210                 215                 220

Asn Asp Glu Lys Arg Gln Pro Pro Glu Lys Lys Ser Lys Leu Phe Ala
225                 230                 235                 240

Met Gly Val Glu Arg Ala Asn Val Gln Ile Gly Tyr Val Met Leu Asn
                245                 250                 255

Thr Leu Cys Ile Arg Glu His Asn Arg Ile Cys Asp Val Leu Ser Lys
                260                 265                 270

Ser Tyr Pro Glu Trp Asp Asp Glu Arg Leu Phe Gln Thr Ala Arg Asn
                275                 280                 285

Ile Leu Met Val Ile Val Leu Asn Ile Ile Met Glu Glu Tyr Ile Phe
290                 295                 300

His Ile Thr Pro Tyr Asn Phe Arg Phe Phe Ala Asp Pro Glu Ala Phe
305                 310                 315                 320

Thr Lys Glu Ser Trp Tyr Arg Glu Asn Trp Met Ala Ile Glu Phe Ser
                325                 330                 335

Phe Val Tyr Arg Trp His Ser Ala Ile Pro Glu Thr Phe Ile Tyr Asp
                340                 345                 350

Gly Lys Glu Gln Ser Met Tyr Asp Ser Leu Trp Asn Asn Gln Met Leu
                355                 360                 365

Ile Asp Lys Gly Leu Gly Ala Leu Met Glu Glu Thr Cys Ser Gln Pro
370                 375                 380

Gly Thr Arg Ile Gly Leu Phe Asn Thr Pro Asp Phe Lys Ile Ala Gly
385                 390                 395                 400

Thr Pro Tyr Thr Phe Ile Asp Ala Thr Glu Leu Ala Ser Val Lys Leu
                405                 410                 415

Gly Arg Gln Ala Gln Leu Ala Ser Tyr Asn Asp Tyr Arg Glu Met Cys
                420                 425                 430

Gly Tyr Pro Arg Val Thr Asp Phe Asn Gln Ile Thr Gly Asp Glu Tyr
                435                 440                 445

Ala Gln Gln Lys Leu Lys Glu Leu Tyr Gly His Val Asp Lys Ile Glu
450                 455                 460

Leu Phe Val Gly Leu Tyr Ala Glu Asp Val Arg Lys Asn Ser Ala Ile
465                 470                 475                 480

Pro Pro Leu Val Ala Arg Ile Ile Gly Ile Asp Ala Phe Ser Gln Ala
                485                 490                 495

Leu Thr Asn Pro Leu Leu Ser Pro Lys Val Phe Asn Lys Glu Thr Phe
                500                 505                 510

Ser Glu Val Gly Trp Glu Ile Ile Gln Asn Thr Lys Thr Val Ser Asp
                515                 520                 525

Leu Val Asn Arg Asn Val Pro Pro Ser Asp Pro Lys Tyr Lys Val Ser
530                 535                 540

Phe Glu Thr

<210> SEQ ID NO 11
<211> LENGTH: 540
<212> TYPE: PRT
<213> ORGANISM: Artificial Sequence
<220> FEATURE:
<223> OTHER INFORMATION: Engineered heme peroxidase

<400> SEQUENCE: 11

```
Arg Asp Thr Ser Lys Asp Gly Phe Arg Asn Lys Leu Glu Thr Tyr Ala
1               5                   10                  15

Leu Thr His Phe Lys Pro Ile Trp Asn Leu Ile Gln Ser Asn Asp Thr
            20                  25                  30

Leu Lys Lys Lys Val Asn Lys Phe Leu Val Asn Asn Ala Ile Tyr Lys
        35                  40                  45

Val Pro Thr Arg Pro Tyr Pro Phe Ser Thr Met Ser Pro Tyr Thr Ser
    50                  55                  60

Trp Asp Ser Leu Ser Asp Arg Thr Tyr Ser Gly Leu His Leu Pro Pro
65                  70                  75                  80

Leu Asp Trp Gln Pro Leu Thr Asn Glu Asn His Leu Lys Leu Lys Leu
                85                  90                  95

Ala Asp Thr Lys Asp Phe Glu Lys Lys Leu Pro Ala Ile Glu Asp Leu
            100                 105                 110

Arg Gly Leu Tyr Arg Lys Ser Gly Glu Thr Lys Tyr Ser Pro Lys Ser
        115                 120                 125

Thr Leu Ile Phe Pro Tyr Phe Val Gln Trp Thr Asp Ser Phe Leu
    130                 135                 140

Arg Thr Asp Arg His Asn His Arg Lys Asn Thr Ser Asn His Gln Ile
145                 150                 155                 160

Asp Leu Cys Thr Val Tyr Gly Leu Asn Ala Lys Ile Thr His Leu Leu
                165                 170                 175

Arg Ser Tyr Gln Gly Gly Lys Leu Lys Ser Gln Ile Ile Asn Gly Glu
            180                 185                 190

Glu Tyr Pro Pro Phe Tyr Tyr Asp Glu Lys Gly Glu Ala Lys Lys Glu
        195                 200                 205

Phe Ile Gly Leu Pro His Gln Leu Asp Asn Asp Gly Asn Pro Lys Ala
    210                 215                 220

Asp Thr Phe Pro Leu Asp Lys Lys Gln Lys Leu Phe Ala Met Gly Val
225                 230                 235                 240

Glu Val Glu Arg Ser Asn Val Gln Ile Gly Tyr Val Met Leu Asn Val
                245                 250                 255

Leu Ala Leu Arg Glu His Asn Arg Leu Cys Glu Leu Leu Ala Lys Thr
            260                 265                 270

Tyr Pro Ser Trp Asp Asp Glu Arg Leu Phe Gln Thr Ala Arg Asn Ile
        275                 280                 285

Leu Ile Val Glu Val Leu Arg Ile Val Val Glu Asp Tyr Val Asn His
    290                 295                 300

Ile Thr Pro Tyr His Phe Gln Phe Ile Thr Asp Pro Leu Thr Phe Ser
305                 310                 315                 320

Asn Glu Lys Trp Tyr Arg Gln Asn Trp Met Thr Val Glu Phe Thr Leu
                325                 330                 335

Val Tyr Arg Trp His Ser Met Leu Pro Asp Thr Leu Ile Tyr Asn Gly
            340                 345                 350

Gln Lys Ile Pro Thr Tyr Glu Thr Gln Trp Asn Asn Glu Met Ile Ile
```

```
                355                 360                 365
Lys Gln Gly Leu Gly Ala Leu Phe Glu Glu Ser Cys Ser Gln Pro Cys
370                 375                 380

Ala Gln Leu Ser Leu Phe Asn Thr Pro Glu Phe Leu Ile Pro Val Glu
385                 390                 395                 400

Leu Ala Ser Val Arg Phe Gly Arg Glu Val Lys Leu Arg Ser Tyr Asn
                405                 410                 415

Asp Tyr Arg Gln Leu Cys Lys Tyr Pro Arg Val Thr Asp Phe Asp Gln
            420                 425                 430

Ile Ser Ser Asp Lys Asn Ile Gln Lys Glu Leu Gln Arg Leu Tyr Gly
        435                 440                 445

His Val Asp Asn Ile Glu Leu Tyr Val Gly Ile Tyr Ala Glu Asp Leu
    450                 455                 460

Arg Glu Asn Ser Ala Leu Pro Ser Leu Val Gly Arg Leu Ile Gly Ile
465                 470                 475                 480

Asp Ala Phe Ser Gln Val Leu Thr Asn Pro Leu Leu Ala Glu Ser Val
                485                 490                 495

Phe His Pro Glu Thr Phe Ser Pro Val Gly Trp Glu Ile Gln Asn
            500                 505                 510

Thr Lys Thr Leu Ser Gln Leu Leu His Arg Asn Leu Pro Pro Ser Asp
        515                 520                 525

Lys Lys Tyr Arg Val Ser Phe Asp Arg Ala Ser Leu
    530                 535                 540

<210> SEQ ID NO 12
<211> LENGTH: 543
<212> TYPE: PRT
<213> ORGANISM: Artificial Sequence
<220> FEATURE:
<223> OTHER INFORMATION: Engineered heme peroxidase

<400> SEQUENCE: 12

Ala Gly Lys Arg Asp Thr Ser Lys Asp Gly Phe Asp Asn Lys Val Gln
1               5                   10                  15

Thr Phe Leu Leu Thr Asn Phe Lys Gly Ile Trp Glu Ile Val Gln Ser
            20                  25                  30

Asn Glu Phe Leu Lys Arg Lys Val Asn Lys Thr Leu Ile Asn Ser Leu
        35                  40                  45

Ile Tyr Lys Ile Pro Thr Arg Pro Asn Pro Tyr Ser Met Met Thr Leu
    50                  55                  60

Asp Glu Tyr Ile Pro Asp Thr Lys Ile Pro Lys Lys Thr Asp Thr Tyr
65                  70                  75                  80

Thr Ser Trp Glu Leu Leu Asn Asp Arg Thr Tyr Ile Gly Arg His Leu
                85                  90                  95

Pro Pro Asp Pro Lys Phe Asn Ser Glu Gly Asn Leu Pro Lys Val Glu
            100                 105                 110

Asp Leu Ala Val Leu Phe Arg Lys Arg Asp Gly Lys Thr Ile Tyr Ser
        115                 120                 125

Pro Lys Ser Thr Met Leu Phe Pro Tyr Trp Val Gln Trp Phe Thr Asp
    130                 135                 140

Ser Phe Leu Arg Ile Asp His Thr Lys Glu Lys Lys Leu Lys Asn Thr
145                 150                 155                 160

Ser Asn His Glu Ile Asp Leu Cys Asn Val Tyr Gly Leu Asn Arg Lys
                165                 170                 175

Arg Thr His Leu Leu Arg Thr Phe Lys Gly Gly Lys Phe Lys Thr Gln
```

```
                    180                 185                 190
Lys Leu Lys Arg Gln Asp Gly Ile Glu Glu Tyr Pro Leu Phe Tyr
            195                 200                 205

Tyr Ala Asp Pro Ala Gln Gly Ile Val Asp Pro Gln Phe Asp Gly Leu
210                 215                 220

Tyr Glu Pro Ile Asn Asp Glu Lys Arg Leu Pro Ala Asp Lys Lys Gln
225                 230                 235                 240

Tyr Leu Phe Ala Met Gly Val Glu Arg Ala Asn Val Gln Ile Gly Tyr
            245                 250                 255

Val Met Leu Asn Thr Leu Cys Ile Arg Glu His Asn Arg Leu Cys Asp
            260                 265                 270

Glu Leu Ala Ser Asn Tyr Pro Asp Trp Asp Asp Glu Arg Leu Phe Gln
            275                 280                 285

Thr Ser Arg Asn Ile Leu Met Ala Ile Ile Leu Asn Ile Ile Met Glu
            290                 295                 300

Glu Tyr Ile Asn His Ile Thr Pro Tyr His Phe Lys Leu Phe Ala Asp
305                 310                 315                 320

Pro Ala Ala Phe Val Lys Glu Ser Trp Tyr Arg Pro Asn Trp Met Thr
                325                 330                 335

Ile Glu Phe Asp Phe Val Tyr Arg Trp His Ser Ala Ile Pro Glu Thr
                340                 345                 350

Phe Ile Tyr Asp Gly Gln Pro Thr Asp Ile Ala Ala Ser Leu Trp Asn
            355                 360                 365

Asn Lys Met Phe Ile Asp Lys Gly Leu Gly Ala Leu Met Glu Glu Thr
            370                 375                 380

Cys Ser Gln Pro Gly Thr Arg Ile Gly Leu Phe Asn Thr Pro Asp Ile
385                 390                 395                 400

Leu Val Glu Leu Thr Glu Leu Pro Ser Ile Arg Leu Gly Arg Gln Leu
                405                 410                 415

Gln Leu Ala Ser Tyr Asn Asp Tyr Arg Glu Met Cys Gly Phe Pro Arg
            420                 425                 430

Val Thr Lys Phe Glu Gln Ile Thr Gly Asp Glu Phe Ala Gln Glu Lys
            435                 440                 445

Leu Lys Glu Leu Tyr Gly His Val Asp Asn Ile Glu Phe Tyr Val Gly
            450                 455                 460

Leu Tyr Ala Glu Glu Val Arg Lys Asn Ser Thr Ile Pro Pro Leu Val
465                 470                 475                 480

Ala Arg Leu Ile Gly Ile Asp Ala Phe Ser Glu Ala Leu Asn Asn Pro
                485                 490                 495

Leu Leu Ser Pro Thr Ile Phe Asn Lys Asp Thr Phe Ser Pro Val Gly
                500                 505                 510

Trp Glu Ile Ile Gln Asn Thr Lys Thr Val Ser Asp Leu Ile Asn Arg
            515                 520                 525

Asn Val Pro Pro Ser Asp Lys Lys Tyr Lys Val Thr Phe Asp Thr
            530                 535                 540

<210> SEQ ID NO 13
<211> LENGTH: 547
<212> TYPE: PRT
<213> ORGANISM: Artificial Sequence
<220> FEATURE:
<223> OTHER INFORMATION: Consensus prostaglandin-endoperoxide synthase
      sequence
<220> FEATURE:
<221> NAME/KEY: misc_feature
<222> LOCATION: (547)..(547)
```

<223> OTHER INFORMATION: Xaa can be any naturally occurring amino acid

<400> SEQUENCE: 13

```
Thr Arg Asp Thr Ser Arg Asp Gly Phe Ser Asn Lys Ala Leu Ala Tyr
1               5                   10                  15
Thr Leu Thr His Phe Lys Pro Ile Trp Asn Leu Val Gln Ser Tyr Glu
            20                  25                  30
Pro Leu Lys Arg Lys Leu Asn Lys Phe Phe Leu Asn Ser Ile Ile Tyr
        35                  40                  45
Lys Leu Pro Thr Arg Pro Leu Pro Tyr Ser Leu Met Gly Leu Asp Pro
    50                  55                  60
Lys Ile Pro Gly Thr Asp Ile Pro Lys Lys Thr Asp Thr Tyr Ile Ser
65                  70                  75                  80
Trp Asp Ser Leu Thr Asp Lys Thr Tyr Thr Gly Arg His Leu Pro Pro
                85                  90                  95
Asp Pro Glu Phe Asn Lys Glu Gly Asn Leu Pro Pro Leu Asp Lys Val
            100                 105                 110
Lys Thr Leu Phe Gln Lys Arg Asp Gly Lys Thr Ile Tyr Ser Glu Lys
        115                 120                 125
Ser Thr Leu Leu Phe Pro Tyr Trp Val Gln Trp Phe Thr Asp Ser Phe
    130                 135                 140
Leu Arg Ile Asp Gln Glu Asn Arg Phe Lys Asn Thr Ser Asn His Gln
145                 150                 155                 160
Ile Asp Met Cys Asn Val Tyr Gly Leu Thr Arg Lys Gln Thr Asn Met
                165                 170                 175
Leu Arg Ala Phe Lys Asp Gly Lys Phe Lys Thr Gln Lys Leu Lys Arg
            180                 185                 190
Lys Asp Gly Val Glu Glu Glu Tyr Pro Leu Phe Tyr Tyr Ala Asp Pro
        195                 200                 205
Glu Gln Gly Ile Ile Asp Pro Gln Phe Glu Gly Leu His Ala Pro Leu
    210                 215                 220
Asn Asp Glu Lys Arg Gln Pro Pro Glu Lys Lys Ser Lys Leu Phe Ala
225                 230                 235                 240
Met Gly Val Glu Arg Ala Asn Val Gln Ile Gly Tyr Val Met Leu Asn
                245                 250                 255
Thr Leu Cys Ile Arg Glu His Asn Arg Ile Cys Asp Val Leu Ser Lys
            260                 265                 270
Ser Tyr Pro Glu Trp Asp Asp Glu Arg Leu Phe Gln Thr Ala Arg Asn
        275                 280                 285
Ile Leu Met Val Ile Val Leu Asn Ile Ile Met Glu Glu Tyr Ile Phe
    290                 295                 300
His Ile Thr Pro Tyr Asn Phe Arg Phe Ala Asp Pro Glu Ala Phe Phe
305                 310                 315                 320
Thr Lys Glu Ser Trp Tyr Arg Glu Asn Trp Met Ala Ile Glu Phe Ser
                325                 330                 335
Phe Val Tyr Arg Trp His Ser Ala Ile Pro Glu Thr Phe Ile Tyr Asp
            340                 345                 350
Gly Lys Glu Gln Ser Met Tyr Asp Ser Leu Trp Asn Asn Gln Met Leu
        355                 360                 365
Ile Asp Lys Gly Leu Gly Ala Leu Met Glu Glu Thr Cys Ser Gln Pro
    370                 375                 380
Gly Thr Arg Ile Gly Leu Phe Asn Thr Pro Asp Phe Lys Ile Ala Gly
385                 390                 395                 400
```

```
Thr Pro Tyr Thr Phe Ile Asp Ala Thr Glu Leu Ala Ser Val Lys Leu
                405                 410                 415
Gly Arg Gln Ala Gln Leu Ala Ser Tyr Asn Asp Tyr Arg Glu Met Cys
            420                 425                 430
Gly Tyr Pro Arg Val Thr Asp Phe Asn Gln Ile Thr Gly Asp Glu Tyr
            435                 440                 445
Ala Gln Gln Lys Leu Lys Glu Leu Tyr Gly His Val Asp Lys Ile Glu
    450                 455                 460
Leu Phe Val Gly Leu Tyr Ala Glu Asp Val Arg Lys Asn Ser Ala Ile
465                 470                 475                 480
Pro Pro Leu Val Ala Arg Ile Ile Gly Ile Asp Ala Phe Ser Gln Ala
                485                 490                 495
Leu Thr Asn Pro Leu Leu Ser Pro Lys Val Phe Asn Lys Glu Thr Phe
                500                 505                 510
Ser Glu Val Gly Trp Glu Ile Ile Gln Asn Thr Lys Thr Val Ser Asp
                515                 520                 525
Leu Val Asn Arg Asn Val Pro Pro Ser Asp Pro Lys Tyr Lys Val Ser
                530                 535                 540
Phe Glu Xaa
545

<210> SEQ ID NO 14
<211> LENGTH: 540
<212> TYPE: PRT
<213> ORGANISM: Artificial Sequence
<220> FEATURE:
<223> OTHER INFORMATION: Consensus heme peroxide sequence
<220> FEATURE:
<221> NAME/KEY: misc_feature
<222> LOCATION: (540)..(540)
<223> OTHER INFORMATION: Xaa can be any naturally occurring amino acid

<400> SEQUENCE: 14

Arg Asp Thr Ser Lys Asp Gly Phe Arg Asn Lys Leu Glu Thr Tyr Ala
1               5                   10                  15
Leu Thr His Phe Lys Pro Ile Trp Asn Leu Ile Gln Ser Asn Asp Thr
                20                  25                  30
Leu Lys Lys Lys Val Asn Lys Phe Leu Val Asn Asn Ala Ile Tyr Lys
            35                  40                  45
Val Pro Thr Arg Pro Tyr Pro Phe Ser Thr Met Ser Pro Tyr Thr Ser
    50                  55                  60
Trp Asp Ser Leu Ser Asp Arg Thr Tyr Ser Gly Leu His Leu Pro Pro
65                  70                  75                  80
Leu Asp Trp Gln Pro Leu Thr Asn Glu Asn His Leu Lys Leu Lys Leu
                85                  90                  95
Ala Asp Thr Lys Asp Phe Glu Lys Lys Leu Pro Ala Ile Glu Asp Leu
                100                 105                 110
Arg Gly Leu Tyr Arg Lys Ser Gly Glu Thr Lys Tyr Ser Pro Lys Ser
            115                 120                 125
Thr Leu Ile Phe Pro Tyr Phe Val Gln Trp Phe Thr Asp Ser Phe Leu
    130                 135                 140
Arg Thr Asp Arg His Asn His Arg Lys Asn Thr Ser Asn His Gln Ile
145                 150                 155                 160
Asp Leu Cys Thr Val Tyr Gly Leu Asn Ala Lys Ile Thr His Leu Leu
                165                 170                 175
Arg Ser Tyr Gln Gly Gly Lys Leu Lys Ser Gln Ile Ile Asn Gly Glu
                180                 185                 190
```

```
Glu Tyr Pro Pro Phe Tyr Tyr Asp Glu Lys Gly Glu Ala Lys Lys Glu
            195                 200                 205

Phe Ile Gly Leu Pro His Gln Leu Asp Asn Asp Gly Asn Pro Lys Ala
210                 215                 220

Asp Thr Phe Pro Leu Asp Lys Lys Gln Lys Leu Phe Ala Met Gly Val
225                 230                 235                 240

Glu Val Glu Arg Ser Asn Val Gln Ile Gly Tyr Val Met Leu Asn Val
            245                 250                 255

Leu Ala Leu Arg Glu His Asn Arg Leu Cys Glu Leu Leu Ala Lys Thr
            260                 265                 270

Tyr Pro Ser Trp Asp Asp Glu Arg Leu Phe Gln Thr Ala Arg Asn Ile
            275                 280                 285

Leu Ile Val Glu Val Leu Arg Ile Val Val Glu Asp Tyr Val Asn His
            290                 295                 300

Ile Thr Pro Tyr His Phe Gln Phe Ile Thr Asp Pro Leu Thr Phe Ser
305                 310                 315                 320

Asn Glu Lys Trp Tyr Arg Gln Asn Trp Met Thr Val Glu Phe Thr Leu
            325                 330                 335

Val Tyr Arg Trp His Ser Met Leu Pro Asp Thr Leu Ile Tyr Asn Gly
            340                 345                 350

Gln Lys Ile Pro Thr Tyr Glu Thr Gln Trp Asn Asn Glu Met Ile Ile
            355                 360                 365

Lys Gln Gly Leu Gly Ala Leu Phe Glu Glu Ser Cys Ser Gln Pro Cys
370                 375                 380

Ala Gln Leu Ser Leu Phe Asn Thr Pro Glu Phe Leu Ile Pro Val Glu
385                 390                 395                 400

Leu Ala Ser Val Arg Phe Gly Arg Glu Val Lys Leu Arg Ser Tyr Asn
            405                 410                 415

Asp Tyr Arg Gln Leu Cys Lys Tyr Pro Arg Val Thr Asp Phe Asp Gln
            420                 425                 430

Ile Ser Ser Asp Lys Asn Ile Gln Lys Glu Leu Gln Arg Leu Tyr Gly
            435                 440                 445

His Val Asp Asn Ile Glu Leu Tyr Val Gly Ile Tyr Ala Glu Asp Leu
            450                 455                 460

Arg Glu Asn Ser Ala Leu Pro Ser Leu Val Gly Arg Leu Ile Gly Ile
465                 470                 475                 480

Asp Ala Phe Ser Gln Val Leu Thr Asn Pro Leu Leu Ala Glu Ser Val
            485                 490                 495

Phe His Pro Glu Thr Phe Ser Pro Val Gly Trp Glu Glu Ile Gln Asn
            500                 505                 510

Thr Lys Thr Leu Ser Gln Leu Leu His Arg Asn Leu Pro Pro Ser Asp
            515                 520                 525

Lys Lys Tyr Arg Val Ser Phe Asp Arg Ala Ser Xaa
530                 535                 540

<210> SEQ ID NO 15
<211> LENGTH: 544
<212> TYPE: PRT
<213> ORGANISM: Artificial Sequence
<220> FEATURE:
<223> OTHER INFORMATION: Consensus heme peroxide sequence
<220> FEATURE:
<221> NAME/KEY: misc_feature
<222> LOCATION: (544)..(544)
<223> OTHER INFORMATION: Xaa can be any naturally occurring amino acid
```

<400> SEQUENCE: 15

```
Ala Gly Lys Arg Asp Thr Ser Lys Asp Gly Phe Asp Asn Lys Val Gln
 1               5                  10                  15

Thr Phe Leu Leu Thr Asn Phe Lys Gly Ile Trp Glu Ile Val Gln Ser
             20                  25                  30

Asn Glu Phe Leu Lys Arg Lys Val Asn Lys Thr Leu Ile Asn Ser Leu
         35                  40                  45

Ile Tyr Lys Ile Pro Thr Arg Pro Asn Pro Tyr Ser Met Met Thr Leu
     50                  55                  60

Asp Glu Tyr Ile Pro Asp Thr Lys Ile Pro Lys Lys Thr Asp Thr Tyr
 65                  70                  75                  80

Thr Ser Trp Glu Leu Leu Asn Asp Arg Thr Tyr Ile Gly Arg His Leu
             85                  90                  95

Pro Pro Asp Pro Lys Phe Asn Ser Glu Gly Asn Leu Pro Lys Val Glu
        100                 105                 110

Asp Leu Ala Val Leu Phe Arg Lys Arg Asp Gly Lys Thr Ile Tyr Ser
    115                 120                 125

Pro Lys Ser Thr Met Leu Phe Pro Tyr Trp Val Gln Trp Phe Thr Asp
    130                 135                 140

Ser Phe Leu Arg Ile Asp His Thr Lys Glu Lys Leu Lys Asn Thr
145                 150                 155                 160

Ser Asn His Glu Ile Asp Leu Cys Asn Val Tyr Gly Leu Asn Arg Lys
            165                 170                 175

Arg Thr His Leu Leu Arg Thr Phe Lys Gly Lys Phe Lys Thr Gln
        180                 185                 190

Lys Leu Lys Arg Gln Asp Gly Ile Glu Glu Tyr Pro Leu Phe Tyr
    195                 200                 205

Tyr Ala Asp Pro Ala Gln Gly Ile Val Asp Pro Gln Phe Asp Gly Leu
    210                 215                 220

Tyr Glu Pro Ile Asn Asp Glu Lys Arg Leu Pro Ala Asp Lys Lys Gln
225                 230                 235                 240

Tyr Leu Phe Ala Met Gly Val Glu Arg Ala Asn Val Gln Ile Gly Tyr
            245                 250                 255

Val Met Leu Asn Thr Leu Cys Ile Arg Glu His Asn Arg Leu Cys Asp
            260                 265                 270

Glu Leu Ala Ser Asn Tyr Pro Asp Trp Asp Asp Glu Arg Leu Phe Gln
        275                 280                 285

Thr Ser Arg Asn Ile Leu Met Ala Ile Leu Asn Ile Ile Met Glu
    290                 295                 300

Glu Tyr Ile Asn His Ile Thr Pro Tyr His Phe Lys Leu Phe Ala Asp
305                 310                 315                 320

Pro Ala Ala Phe Val Lys Glu Ser Trp Tyr Arg Pro Asn Trp Met Thr
            325                 330                 335

Ile Glu Phe Asp Phe Val Tyr Arg Trp His Ser Ala Ile Pro Glu Thr
        340                 345                 350

Phe Ile Tyr Asp Gly Gln Pro Thr Asp Ile Ala Ala Ser Leu Trp Asn
    355                 360                 365

Asn Lys Met Phe Ile Asp Lys Gly Leu Gly Ala Leu Met Glu Glu Thr
    370                 375                 380

Cys Ser Gln Pro Gly Thr Arg Ile Gly Leu Phe Asn Thr Pro Asp Ile
385                 390                 395                 400

Leu Val Glu Leu Thr Glu Leu Pro Ser Ile Arg Leu Gly Arg Gln Leu
            405                 410                 415
```

```
-continued

Gln Leu Ala Ser Tyr Asn Asp Tyr Arg Glu Met Cys Gly Phe Pro Arg
            420                 425                 430

Val Thr Lys Phe Glu Gln Ile Thr Gly Asp Glu Phe Ala Gln Glu Lys
        435                 440                 445

Leu Lys Glu Leu Tyr Gly His Val Asp Asn Ile Glu Phe Tyr Val Gly
    450                 455                 460

Leu Tyr Ala Glu Glu Val Arg Lys Asn Ser Thr Ile Pro Pro Leu Val
465                 470                 475                 480

Ala Arg Leu Ile Gly Ile Asp Ala Phe Ser Glu Ala Leu Asn Asn Pro
                485                 490                 495

Leu Leu Ser Pro Thr Ile Phe Asn Lys Asp Thr Phe Ser Pro Val Gly
            500                 505                 510

Trp Glu Ile Ile Gln Asn Thr Lys Thr Val Ser Asp Leu Ile Asn Arg
        515                 520                 525

Asn Val Pro Pro Ser Asp Lys Lys Tyr Lys Val Thr Phe Asp Leu Xaa
    530                 535                 540
```